US012285634B2

(12) United States Patent
Eldered et al.

(10) Patent No.: US 12,285,634 B2
(45) Date of Patent: Apr. 29, 2025

(54) RADIOTHERAPY APPARATUS FOR DELIVERING RADIATION TO A SUBJECT

(71) Applicant: Elekta Limited, Crawley (GB)

(72) Inventors: Kjell Eldered, Crawley (GB); Kristian Wiberg, Crawley (GB)

(73) Assignee: Elekta Limited, Crawley (GB)

( * ) Notice: Subject to any disclaimer, the term of this patent is extended or adjusted under 35 U.S.C. 154(b) by 273 days.

(21) Appl. No.: 17/757,675

(22) PCT Filed: Dec. 17, 2020

(86) PCT No.: PCT/EP2020/086663
§ 371 (c)(1),
(2) Date: Jun. 17, 2022

(87) PCT Pub. No.: WO2021/122908
PCT Pub. Date: Jun. 24, 2021

(65) Prior Publication Data
US 2022/0339469 A1   Oct. 27, 2022

(30) Foreign Application Priority Data
Dec. 18, 2019   (GB) ..................... 1918757

(51) Int. Cl.
*A61N 5/00* (2006.01)
*A61G 13/04* (2006.01)
(Continued)

(52) U.S. Cl.
CPC ........... *A61N 5/1081* (2013.01); *A61G 13/04* (2013.01); *A61G 13/06* (2013.01); *A61N 5/1049* (2013.01); *A61G 2210/00* (2013.01); *A61N 5/103* (2013.01)

(58) Field of Classification Search
CPC ...................................................... A61N 5/10
See application file for complete search history.

(56) References Cited

U.S. PATENT DOCUMENTS

| 6,094,760 | A  | 8/2000 | Nonaka et al. |
| 10,695,586 | B2 | 6/2020 | Harper et al. |

(Continued)

FOREIGN PATENT DOCUMENTS

| CN | 106456991 | 2/2017 |
| CN | 108325093 | 7/2018 |

(Continued)

OTHER PUBLICATIONS

U.S. Appl. No. 17/757,674, filed Jun. 17, 2022, Radiotherapy Apparatus for Delivering Radiation to a Subject.
(Continued)

*Primary Examiner* — Dani Fox
(74) *Attorney, Agent, or Firm* — Schwegman Lundberg & Woessner, P.A.

(57) ABSTRACT

The present application relates to a radiotherapy apparatus for delivering radiation to a subject. The apparatus comprises a source of radiation configured to rotate about an isocenter and emit radiation in a radiation plane containing said isocentre. The apparatus also comprises a subject support surface including a portion configured to be located substantially at the isocenter. The subject support surface comprises a subject support surface rotation mechanism configured to rotate the subject support surface about an axis of rotation parallel to and spaced from an axis that passes through the isocenter. The subject support surface also comprises a first section configured to move from a first position to a second position along at least one of a longitudinal and lateral direction. The apparatus also comprises a processor configured to control the longitudinal and/or lateral movement of the first section as a function of the rotation of the subject support surface to maintain the portion of the subject support surface substantially at the isocenter.

13 Claims, 15 Drawing Sheets

(51) Int. Cl.
*A61G 13/06* (2006.01)
*A61N 5/10* (2006.01)

(56) References Cited

U.S. PATENT DOCUMENTS

| | | |
|---|---|---|
| 2004/0098804 A1 | 5/2004 | Varadharajulu et al. |
| 2004/0261176 A1 | 12/2004 | Plannerer |
| 2006/0193443 A1 | 8/2006 | Reger |
| 2007/0023066 A1 | 2/2007 | Yokokawa et al. |
| 2007/0230660 A1 | 10/2007 | Herrmann |
| 2010/0104159 A1 | 4/2010 | Hirokawa et al. |
| 2011/0199085 A1 | 8/2011 | Allen et al. |
| 2011/0211665 A1 | 9/2011 | Maurer, Jr. et al. |
| 2011/0313228 A1 | 12/2011 | Handa et al. |
| 2012/0150018 A1 | 6/2012 | Yamaya et al. |
| 2013/0111668 A1 | 5/2013 | Wiggers et al. |
| 2013/0158382 A1 | 6/2013 | Chao |
| 2014/0171725 A1 | 6/2014 | Adler et al. |
| 2014/0275697 A1* | 9/2014 | Filiberti ............. A61N 5/107 |
| | | 128/845 |
| 2015/0352373 A1 | 12/2015 | Subrahmanyam et al. |
| 2016/0095558 A1 | 4/2016 | Choy et al. |
| 2017/0258414 A1 | 9/2017 | Guertin et al. |
| 2017/0340903 A1 | 11/2017 | Ie et al. |
| 2018/0085603 A1 | 3/2018 | Kruesi et al. |
| 2018/0133518 A1 | 5/2018 | Harper et al. |
| 2018/0154183 A1 | 6/2018 | Sahadevan |
| 2018/0280733 A1 | 10/2018 | Weidlich et al. |
| 2018/0339172 A1 | 11/2018 | Stahl et al. |
| 2020/0043624 A1 | 2/2020 | Schnarr et al. |
| 2021/0031055 A1 | 2/2021 | Jiang et al. |
| 2021/0186789 A1 | 6/2021 | Campbell et al. |
| 2023/0025744 A1 | 1/2023 | Feng et al. |
| 2023/0028350 A1 | 1/2023 | Carlander et al. |
| 2023/0031538 A1 | 2/2023 | Alexis et al. |

FOREIGN PATENT DOCUMENTS

| | | |
|---|---|---|
| JP | 06224 | 1/1994 |
| JP | 10127793 A | 5/1998 |
| JP | 2002325854 | 11/2002 |
| WO | 0232312 | 4/2002 |
| WO | 2007018646 | 2/2007 |
| WO | 2007127970 | 11/2007 |
| WO | 2011088399 | 7/2011 |
| WO | 2018093937 | 5/2018 |

OTHER PUBLICATIONS

U.S. Appl. No. 17/757,678, filed Jun. 17, 2022, Patient Support Apparatus.
U.S. Appl. No. 17/757,682, filed Jun. 17, 2022, Beam Stopper for a Radiotherapy Device.
"International Application Serial No. PCT/EP2020/086663, International Search Report dated Apr. 14, 2021", (Apr. 14, 2021), 3 pgs.
"International Application Serial No. PCT/EP2020/086663, Written Opinion dated Apr. 14, 2021", (Apr. 14, 2021), 5 pgs.
"United Kingdom Application Serial No. 1918757.4, Examination Report dated Jun. 17, 2020", (Jun. 17, 2020), 7 pgs.
"U.S. Appl. No. 17/757,674 Preliminary Amendment Filed with Application", 8 pgs.
"U.S. Appl. No. 17/757,678 Preliminary Amendment Filed with Application", 10 pgs.
"U.S. Appl. No. 17/757,682 Preliminary Amendment Filed with Application", 8 pgs.
"United Kingdom Application Serial No. 1918753.3, Examination Report mailed Aug. 23, 2022", 1 pg.
"United Kingdom GB1918757.4, Examination Report under Section 18(3) mailed Dec. 22, 2022", (Dec. 22, 2022), 4 pgs.
"International Application Serial No. PCT EP2020 086650, International Search Report dated Jun. 24, 2021", (Jun. 24, 2021), 6 pgs.
"International Application Serial No. PCT EP2020 086650, Written Opinion dated Jun. 24, 2021", (Jun. 24, 2021), 8 pgs.
"United Kingdom Application Serial No. 1918753.3, Examination Report dated Dec. 9, 2020", (Dec. 9, 2020), 3 pgs.
"European Application Serial No. 1918757.4, European Search Report dated Jun. 17, 2020", (Jun. 17, 2020), 7 pgs.
"International Application Serial No. PCT EP2020 087307, International Search Report dated Apr. 26, 2021", (Apr. 26, 2021), 3 pgs.
"International Application Serial No. PCT EP2020 087307, Written Opinion dated Apr. 26, 2021", (Apr. 26, 2021), 6 pgs.
"International Application Serial No. PCT CN2020 131937, International Search Report dated Mar. 1, 2021", (Mar. 1, 2021), 4 pgs.
"International Application Serial No. PCT CN2020 131937, Written Opinion dated Mar. 1, 2021", (Mar. 1, 2021), 6 pgs.
"European Application Serial No. 20902566.7, European Search Report dated Jan. 5, 2024", (Jan. 5, 2024), 7 pgs.
"U.S. Appl. No. 17/757,682, Non Final Office Action mailed Jun. 21, 2024", 15 pgs.
"U.S. Appl. No. 17/757,674, Restriction Requirement mailed Aug. 7, 2024", 6 pgs.
"U.S. Appl. No. 17/757,682, Response filed Sep. 20, 2024 to Non Final Office Action mailed Jun. 21, 2024", 13 pgs.
"U.S. Appl. No. 17/757,674, Response filed Oct. 2, 2024 to Restriction Requirement mailed Aug. 7, 2024", 10 pgs.
"U.S. Appl. No. 17/757,682, Final Office Action mailed Oct. 15, 2024", 13 pgs.
"U.S. Appl. No. 17/757,674, Non Final Office Action mailed Nov. 18, 2024", 22 pgs.
"U.S. Appl. No. 17/757,678, Restriction Requirement mailed Nov. 25, 2024", 7 pgs.
"U.S. Appl. No. 17/757,682, Response filed Dec. 16, 2024 to Final Office Action mailed Oct. 15, 2024", 11 pgs.

* cited by examiner

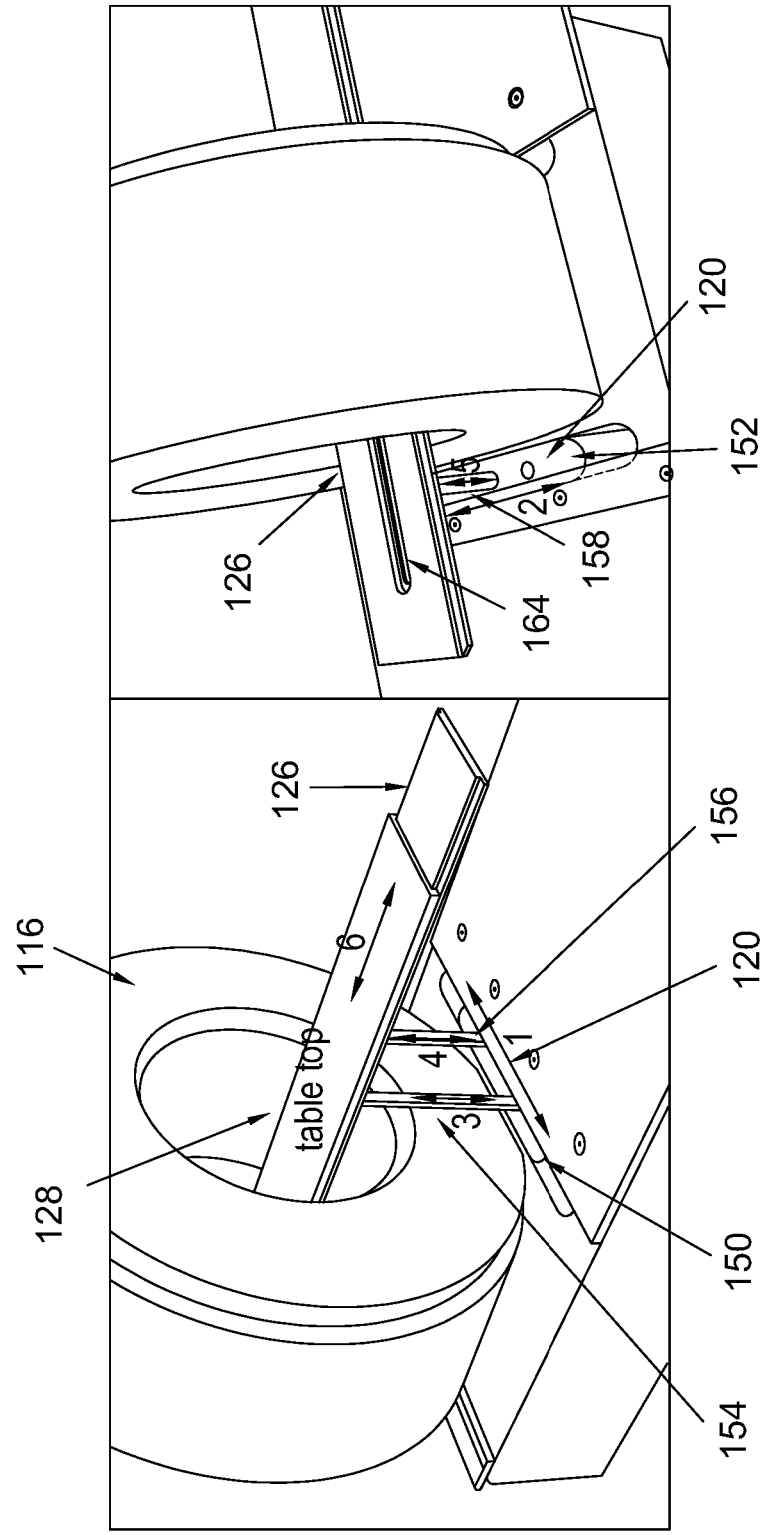

RADIOTHERAPY APPARATUS FOR DELIVERING RADIATION TO A SUBJECT

PRIORITY APPLICATIONS

This application is a U.S. National Stage Filing under 35 U.S.C. § 371 from International Application No. PCT/EP2020/086663, filed on Dec. 17, 2020, and published as WO2021/122908 on Jun. 24, 2021, which claims the benefit of priority to United Kingdom Application No. 1918757.4, filed on Dec. 18, 2019; the benefit of priority of each of which is hereby claimed herein, and which applications and publication are hereby incorporated herein by reference in their entireties.

This disclosure relates generally to a radiotherapy apparatus, and in particular to positioning a subject during the delivery or application of radiotherapy.

BACKGROUND

Radiotherapy uses ionising radiation to treat a human or animal body. In particular, radiotherapy is commonly used to treat tumours within the human or animal body. In such treatments, cells forming part of the tumour are irradiated by ionising radiation in order to destroy or damage them. However, in order to apply a prescribed dose of ionising radiation to a target location or target region, such as a tumour, the ionising radiation will typically also pass through healthy tissue of the human or animal body. Therefore, radiotherapy has the desirable consequence of irradiating and damaging a target region, but can also have the undesirable consequence of irradiating and damaging healthy tissue. In radiotherapy treatment, it is desirable to align the dose received by the target region with a prescribed dose and to minimise the dose received by healthy tissue.

Modern radiotherapy treatment uses techniques to reduce the radiation dose to healthy tissue and thereby provide a safe treatment. For example, one approach to minimising a radiation dose received by healthy tissue surrounding a target region is to direct the radiation towards the target region from a plurality of different angles, for example by rotating a source of radiation around the patient by use of a rotating gantry. In this case, the angles at which radiation is applied are selected such that each beam of radiation passes through the target region. In this way, a cumulative radiation dose may be built up at the target region over the course of a treatment arc in which the radiation source rotates through a certain angle. Radiation is emitted in a radiation plane which is co-incident with the plane of the gantry around which the radiation source rotates and radiation may thus be delivered to a radiation isocenter at the centre of the gantry regardless of the angle to which the radiation head is rotated around the gantry. Because the radiation is applied from a plurality of different angles, the same, high, cumulative radiation dose is not built up in the healthy tissue since the specific healthy tissue the radiation passes through varies with angle. Therefore, a unit volume of the healthy tissue receives a reduced radiation dose relative to a unit volume of the target region. Treatments that utilise rotation of the gantry in this manner are known as coplanar. However, after the radiation source has been rotated 180°, it will be appreciated that any subsequent radiation beams begin to pass through regions of healthy tissue which have already been irradiated. This increases the radiation dose applied to healthy tissue. Accordingly, when using such a method the volume of healthy tissue available to spread the radiation dose is relatively small, thus imposing restrictions on the treatment which can be provided by such devices.

Therefore, an alternative approach to minimising the radiation dose received by healthy tissue surrounding a target region is to rotate the patient relative to the plane of radiation. As the angle of the patient varies relative to the plane of the gantry, so does the healthy tissue the radiation passes through. In order to further reduce the radiation dose relative to a unit volume of the target region, it is desirable to provide a treatment that combines both of these rotations. An example of a known device that combines the rotation of the patient with the rotation of the radiation source is shown in FIG. 1. This shows that the patient 140, who is supported on the subject support surface 114, which is also referred to herein as a patient support surface 114, can be rotated whilst the gantry 116 may also rotate about the patient support surface 114. The gantry 116 shown in FIG. 1 is a C-arm gantry or open gantry. The rotation mechanism 117 rotates the gantry 116 about a fixed axis 119. As the gantry 116 is rotated, radiation emitted by a radiation source 106 can sweep out a circle. Radiation can be applied to the patient 140 from a plurality of angles around the circle. The circle may be described as lying in a radiation plane. The radiation axis lies in the radiation plane. The radiation axis makes an angle of 90° with respect to the fixed axis 119.

The rotation mechanism 120 for the patient support surface 114 is located underneath the gantry 116 of the radiotherapy device, while a rotation mechanism for the gantry 116 is located opposite the patient support surface 114. The rotation mechanism 120 for the patient support surface 114 is located underneath the gantry 116 so that the axis of rotation 111 of the patient support surface 114 will be in the radiation plane. In particular, the axis of rotation 111 of the patient support surface passes through the isocenter 124 of the radiotherapy device, so that the patient support surface 114 is rotated about the isocenter 124. When the patient support surface 114 is in its neural position, the axis of rotation of the patient support surface 114 is substantially vertical (perpendicular to the plane of the floor) and this can also be called a vertical axis 111. The longitudinal axis 113 is parallel to long side of the patient support surface 114 in its neutral position and the transverse axis 115 is parallel to the short end of the patient support surface 114 in its neutral position. The rotation mechanism 120 is located within the plane of radiation. Treatments utilising both the rotation of the radiation and the patient 140 are known as non-coplanar treatments.

Some recently developed radiotherapy devices comprise ring-based gantries (or bores), such as that shown in FIG. 2. Typically, the bore of a radiotherapy device is cylindrical. A patient support surface 114 is positioned in the bore such that radiation can be directed toward a patient 140 positioned on the support surface 114. The bore of the apparatus can be formed by a framework, which may otherwise be described as a chassis, a shielding structure, a shell, or a casing. The framework defines the outer surface of the device which the patient 140 sees upon entering the treatment room, as well as defining the inner surface of the bore which the patient 140 sees when positioned inside the bore. The framework also defines a hollow region of annular cross-section in which the gantry 116 can be both rotated and tilted. Thus, the patient 140 is shielded from the rotatable gantry 116. Movement of the gantry 116 is hidden from the patient's view, reducing intimidation and distress which may otherwise be caused if the patient 140 were able to see rotation of the large gantry 116, as they would for an open gantry as shown in FIG. 1, and also reducing the likelihood that the patient can accidentally touch or otherwise interfere with the movement of the gantry 116. This means that the gantry 116 can be rotated quickly, efficiently and safely. Ring-based gantries are also desirable because they increase device stability. The ring-based gantry is supported by the floor and rests upon it. However, the geometry of a ring-based gantry and its connection to the floor makes it impossible to rotate the subject support surface 114 using known systems in such a way as to maintain a portion of the subject support surface 114 substantially at the isocenter 124.

SUMMARY

An invention is set out in the claims.

FIGURES

Specific embodiments are now described, by way of example only, with reference to the drawings, in which:

FIG. 11A depicts an isometric view of an embodiment of the radiotherapy device with a rotation mechanism comprising first and second sliding bases;

FIG. 11B depicts an isometric view of an embodiment of the radiotherapy device with a rotation mechanism comprising first and second sliding bases;

OVERVIEW

Figure 1:
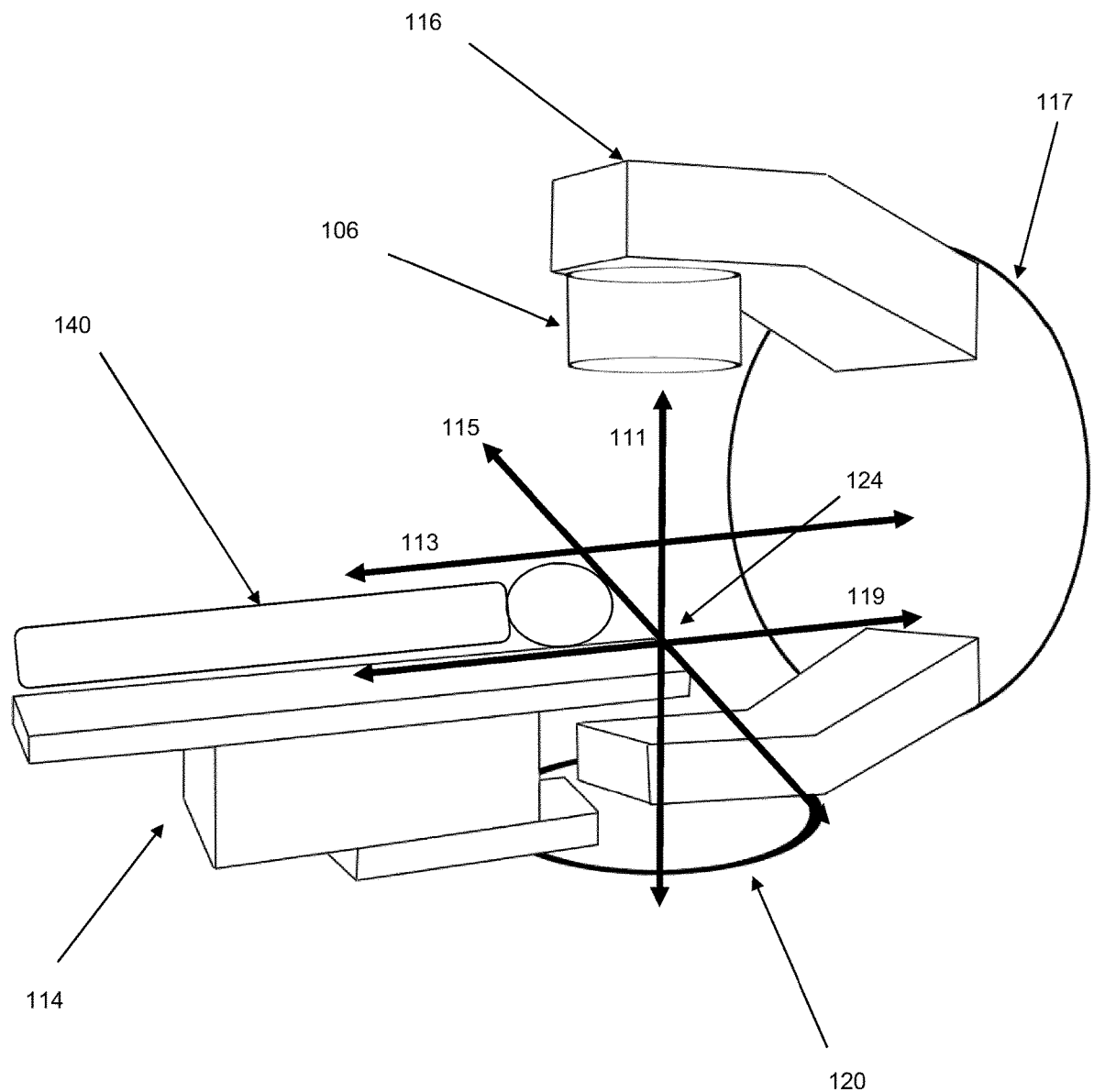
FIG. 1 depicts a known radiotherapy apparatus with rotation means located within the plane of the radiation.
Figure 2:
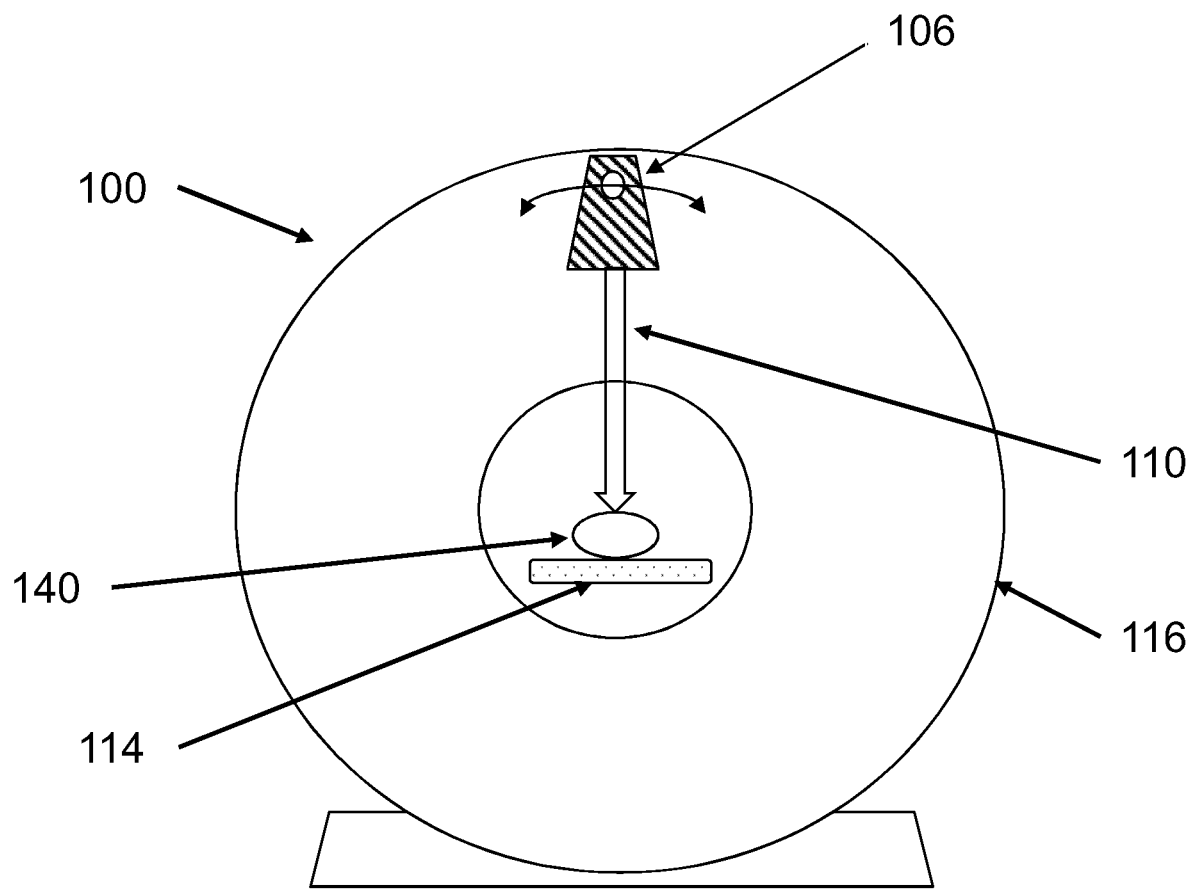
FIG. 2 depicts a front view of a radiotherapy device.

By providing a radiotherapy apparatus for delivering radiation to a subject, the apparatus comprising a source of radiation configured to rotate about an isocenter and emit radiation in a radiation plane containing said isocentre, a subject support surface including a portion configured to be located substantially at the isocenter, the subject support surface comprising a subject support surface rotation mechanism configured to rotate the subject support surface about an axis of rotation parallel to and spaced from an axis that passes through the isocenter and a first section configured to move from a first position to a second position along at least one of a longitudinal and lateral direction, and the apparatus further comprising a processor configured to control the longitudinal and/or lateral movement of the first section as a function of the rotation of the subject support surface to maintain the portion of the subject support surface substantially at the isocenter, a number of benefits are provided.

For example, when the subject support surface/couch is used to support a patient as part of a treatment, the rotation of the subject support surface by the rotation mechanism means that the radiation dose that forms part of the treatment can be spread through the healthy tissue of the patient. Therefore, the total radiation dose received by a particular bit of healthy tissue surrounding a target region can be minimised. At the same time, controlling the movement of the first section as a function to maintain the portion of the subject support surface substantially at the isocenter makes it possible to maximise the amount of radiation that passes through the target region in particular, which increases the efficiency of the treatment. This improves patient wellbeing. The apparatus described herein and locating the rotation mechanism outside the plane of radiation enables the use of a couch kick (rotatable couch) in a ring gantry based linac system.

DETAILED DESCRIPTION

When administering a treatment to a subject or patient 140 with a radiotherapy apparatus comprising a source of radiation 106 configured to rotate about an isocenter 124 and emit radiation in a radiation plane containing said isocenter 124, rotating the subject whilst maintaining the subject substantially at the isocenter 124 allows the dose received by healthy tissue during the radiotherapy treatment to be minimised. This can be achieved by providing a subject support surface rotation mechanism 120 connected to the subject support surface 114 and configured to rotate the subject support surface 114 about an axis of rotation parallel to and spaced apart from an axis that passes through the isocenter 124, whilst moving a top section 128 of the subject support surface 114 to compensate for the relative movement of a particular portion of the subject support surface 114 that is caused by the rotation of the subject support surface 114. In particular, the top section can be moved in a longitudinal and/or lateral direction as a function of the rotation of the subject support surface 114 so as to maintain a portion of the subject support surface 114 substantially at the isocenter 124. By rotating the subject support surface whilst also maintaining a portion of the subject support surface 114 substantially at the isocenter 124 using the movement of a first section (which may be a top section of the subject support surface that is configured to move from a first position to a second position along at least one of a longitudinal and lateral direction independently from the rest of the subject support surface) a number of advantageous effects are achieved. For example, when the apparatus is used for treatment of a patient 140, the radiation dose can be spread through the healthy tissue of the patient 140 so that the radiation dose received by healthy tissue surrounding a target region is minimised. At the same time, it is possible to ensure that the maximum amount of radiation passes through the target region, thereby increasing the efficiency of the treatment. This improves patient 140 wellbeing. If the first section 128 was not configured to move as a function of the rotation of the subject support surface 114 to maintain the portion of the subject support surface 114 substantially at the isocenter 124, then the location of the target region would move with respect to the isocenter 124 (and focus of the radiation) and, accordingly, this would result in an increased dosage of radiation being received by healthy tissue. Furthermore, this would result in a longer treatment time because the target region would not receive the intended dosage of radiation.

The portion of the subject support surface that is maintained substantially at the isocenter 124 may correspond to a portion of a patient 140 such as a target region of a patient 140. Thus, by maintaining a portion of the subject support surface substantially at the isocenter 124 it is possible to maintain a target region substantially at the isocenter 124. Locating the subject support surface rotation mechanism 120 outside the radiation plane allows the dose received by healthy tissue of the subject 140 during the radiotherapy treatment to be minimised for a wide range of radiotherapy apparatuses with different geometries. In particular, the disclosed subject support surface 114 is well suited for radiotherapy apparatuses that comprise a bore for receiving the subject 140.

Figure 3:
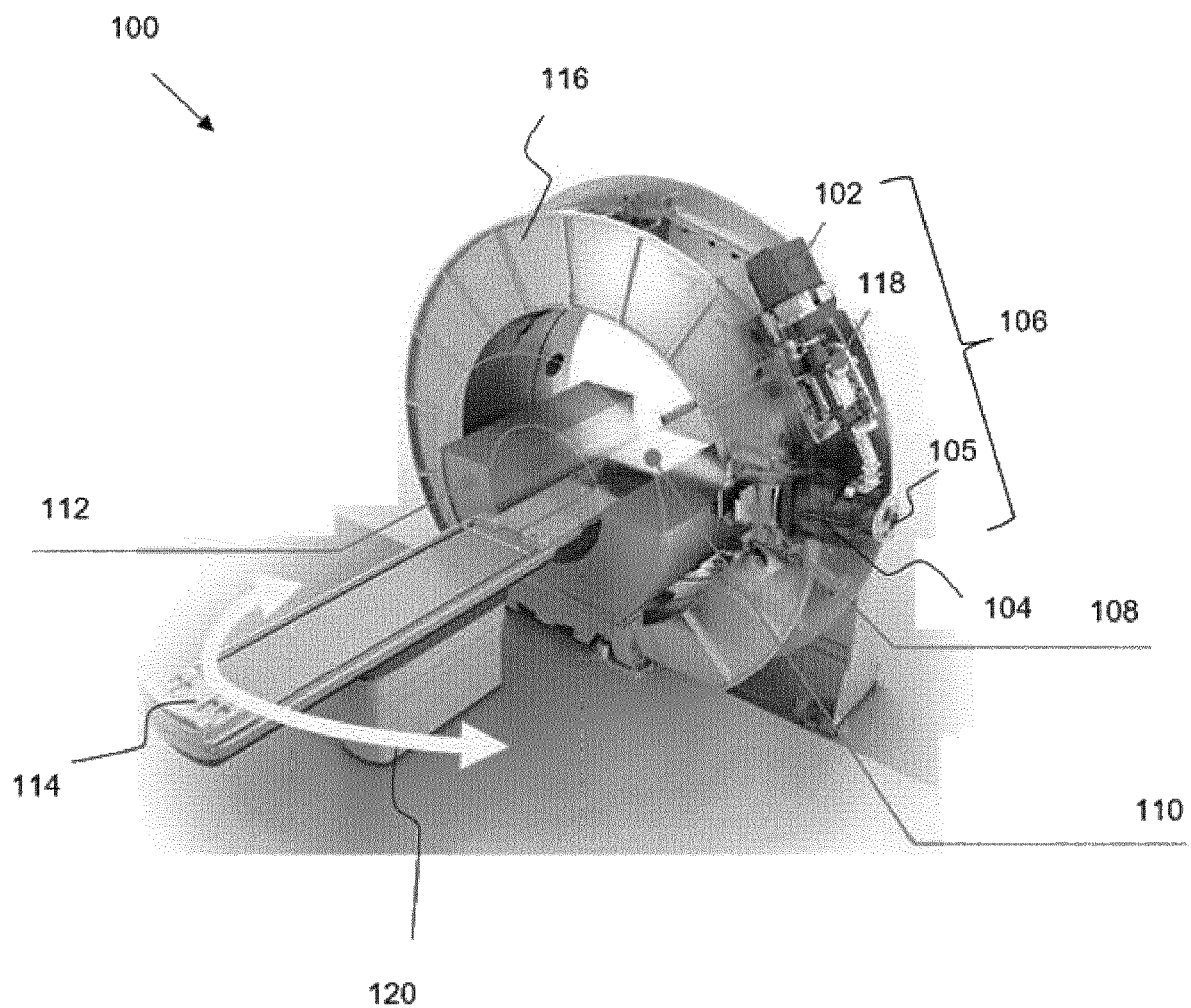
FIG. 3 depicts an isometric view of an embodiment of the radiotherapy device.

In accordance with one embodiment, FIG. 3 depicts a radiotherapy device suitable for delivering a beam of radiation to a patient during radiotherapy treatment. The device and its constituent components will be described generally for the purpose of providing useful accompanying information for the present invention. The device depicted in FIG. 3 is in accordance with the present disclosure and is suitable for use with the disclosed systems and apparatuses, although not all of the features are necessarily present, or as depicted in FIG. 3. While the device in FIG. 3 is an MR-linac, the implementations of the present disclosure may be any radiotherapy device, for example a linac device. FIG. 3 shares features common with known devices such as Versa HD™ in particular, the features involved in producing the treatment beam 110. The embodiment shown in FIG. 3 is modified over known devices in accordance with the invention by the provision of a subject support surface rotation mechanism 120, as will be described in more detail below.

The device depicted in FIG. 3 is an MR-linac. The device comprises both MR imaging apparatus 112 and radiotherapy (RT) apparatus which may comprise a linac device. In operation, the MR scanner produces MR images of the patient 140, and the linac device produces and shapes a beam of radiation and directs it toward a target region within a patient's body in accordance with a radiotherapy treatment plan. The usual 'housing' which would cover the MR imaging apparatus 112 and RT apparatus in a commercial setting such as a hospital is not depicted in FIG. 3.

The MR-linac device depicted in FIG. 3 comprises a source of radiation 106. The source of radiation 106 may comprise beam generation equipment, such as one or more of: a source of radiofrequency waves 102, a circulator 118, a source of electrons 105, a waveguide 104, and a target (not shown) The MR-linac may also comprise a collimator 108 such as a multi-leaf collimator configured to collimate and shape the beam, MR imaging apparatus 112, and a patient support surface 114. The device also comprises a housing which, together with the ring-shaped gantry defines a bore. The moveable subject support surface 114 can be used to move a patient, or other subject, into the bore when an MR scan and/or when radiotherapy is to commence or during treatment. The MR imaging apparatus 112, RT apparatus, and a subject support surface actuator are communicatively coupled to a controller or processor. The controller is also communicatively coupled to a memory device comprising computer-executable instructions which may be executed by the controller.

The RT apparatus comprises a source of radiation 106 and a radiation detector (not shown). Typically, the radiation detector is positioned diametrically opposed to the radiation source 106. The radiation detector is suitable for, and configured to, produce radiation intensity data. In particular, the radiation detector is positioned and configured to detect the intensity of radiation which has passed through the subject. The radiation detector may also be described as radiation detecting means, and may form part of a portal imaging system.

The radiation source 106 defines the point at which the treatment beam 110 is introduced into the bore. The radiation source 106 may comprise a beam generation system, which may comprise a source of RF energy 102, an electron gun 105, and a waveguide 104. The beam generation system is attached to the rotatable gantry 116 so as to rotate with the gantry 116. In this way, the radiation source 106 is rotatable around the patient 140 so that the treatment beam 110 can be applied from different angles around the gantry 116. In a preferred implementation, the gantry 116 is continuously rotatable. In other words, the gantry 116 can be rotated by 360 degrees around the patient, and in fact can continue to be rotated past 360 degrees. The gantry 116 rotates about a mechanical isocenter, which is the point in space about which the gantry 116 rotates and about a fixed axis 119 as shown in FIG. 1. The radiation isocenter can be defined as the point where the radiation beams intersect. These two isocenters 124 need not be the same, although it may be desirable that they should be. In this disclosure, the term isocenter 124 can refer to either or both of these. The isocenter 124 is located within the radiation plane. The gantry 116 may be ring-shaped. In other words, the gantry 116 may be a ring-gantry with a bore. The gantry 116 may also not be ring-shaped and may instead be an open gantry such as that shown in FIG. 1.

The source 102 of radiofrequency waves, such as a magnetron, is configured to produce radiofrequency waves. The source 102 of radiofrequency waves is coupled to the waveguide 104 via circulator 118, and is configured to pulse radiofrequency waves into the waveguide 104. Radiofrequency waves may pass from the source 102 of radiofrequency waves through an RF input window and into an RF input connecting pipe or tube. A source of electrons 105, such as an electron gun, is also coupled to the waveguide 104 and is configured to inject electrons into the waveguide 104. In the source of electrons, electrons are thermionically emitted from a cathode filament as the filament is heated. The temperature of the filament controls the number of electrons injected. The injection of electrons into the waveguide 104 is synchronised with the pumping of the radiofrequency waves into the waveguide 104. The design and operation of the radiofrequency wave source 102, electron source and the waveguide 104 is such that the radiofrequency waves accelerate the electrons to very high energies as the electrons propagate through the waveguide 104.

The source of radiation 106 is configured to direct a beam 110 of therapeutic radiation toward a patient positioned on the patient support surface 114. The source of radiation 106 may comprise a heavy metal target toward which the high energy electrons exiting the waveguide are directed. When the electrons strike the target, X-rays are produced in a variety of directions. A primary collimator may block X-rays travelling in certain directions and pass only forward travelling X-rays to produce a treatment beam 110. The X-rays may be filtered and may pass through one or more ion chambers for dose measuring. The beam can be shaped in various ways by beam-shaping apparatus, for example by using a multi-leaf collimator 108, before it passes into the patient as part of radiotherapy treatment.

In some implementations, the source of radiation 106 is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the linac. In essence, it is possible to swap between the first and second mode by moving the heavy metal target in or out of the electron beam path and replacing it with a so-called 'electron window'. The electron window is substantially transparent to electrons and allows electrons to exit the flight tube.

The radiotherapy apparatus/device depicted in FIG. 3 also comprises MR imaging apparatus 112. The MR imaging apparatus 112 is configured to obtain images of a subject positioned, i.e. located, on the subject support surface 114. The MR imaging apparatus 112 may also be referred to as the MR imager. The MR imaging apparatus 112 may be a conventional MR imaging apparatus 110 operating in a known manner to obtain MR data, for example MR images. The skilled person will appreciate that such a MR imaging apparatus 112 may comprise a primary magnet, one or more gradient coils, one or more receive coils, and an RF pulse applicator. The operation of the MR imaging apparatus is controlled by the controller.

The controller is a computer, processor, or other processing apparatus. The controller may be formed by several discrete processors; for example, the controller may comprise an MR imaging apparatus processor, which controls the MR imaging apparatus 112; an RT apparatus processor, which controls the operation of the RT apparatus; and a subject support surface processor which controls the operation and actuation of the subject support surface. The controller is communicatively coupled to a memory, i.e. a computer readable medium.

The linac device also comprises several other components and systems as will be understood by the skilled person. For example, in order to ensure the linac does not leak radiation, appropriate shielding is also provided.

The patient support surface 114 may serve to support an object. The object may be a human body (such as a patient), an animal body or a material sample. The subject support surface 114 is configured to move parallel to the longitudinal axis 113 between a first position substantially outside the bore, and a second position substantially inside the bore. In the first position, a patient 140 or subject can mount the subject support surface 114. The subject support surface 114, and patient 140, can then be extended inside the bore, to the second position, in order for the patient 140 to be imaged by the MR imaging apparatus 112 and/or imaged or treated using the RT apparatus. The terms subject and patient are used interchangeably herein such that the subject support surface 114 can also be described as a patient support surface 114. The subject support surface 114 may also be referred to herein as a patient support surface and a moveable or adjustable couch or table.

The present invention is distinguished over known devices as follows. The subject support surface 114 is connected to a subject support surface rotation mechanism 120. The rotation mechanism 120 is configured to rotate the subject support surface 114 (which is also described herein as a couch 114, patient support surface 114, or patient positioning system 114) about an axis of rotation parallel to and spaced from an axis that passes through the isocenter 124 of the gantry 116. The rotation mechanism 120 can be attached to the floor or, for example, can be attached to the device housing or gantry 116 (as shown in, for example, FIG. 4a). The patient support surface 114 or part thereof can be rotated around (or about) the longitudinal axis 113 (roll) of the couch 114, around the transverse axis 115 (pitch) of the couch 114, or about an axis perpendicular to the floor 111 (yaw) of the couch 114, whether the couch 114 is in a neutral or a rotated orientation, or any combination of these. These axes are referenced relative to the couch 114, regardless of its orientation at the time, unless specified otherwise.

Although in FIG. 3 the plane of the rotation of the patient support surface 114 is illustrated as being parallel to the illustrated floor (as is defined by the xy plane, which corresponds to the plane of the patient support surface 114 in its neutral position where x is the longitudinal axis 113 and y is the transverse axis 115), with rotation as yaw about the axis 111 of couch 114 in neutral position, by way of example, the angle of the plane of rotation relative to the floor (tilt) could be at an angle of 3, 15, 45 or 90 degrees to the floor. However, for reasons of patient comfort, the angle will usually be kept fairly low. It is also possible for the tilt to be changed either prior to, or during, treatment. The rotation mechanism 120 and/or the patient support surface 114 may also be connected to an additional rotation mechanism (not shown) configured to rotate the rotation mechanism 120 and/or the patient support surface 114 in a different plane. In this way, the patient support surface 114 may be connected to more than one rotation mechanism 120, each configured to move the patient support surface 114 in a different plane. Alternatively, a single rotation mechanism 120 may be configured to rotate the patient support surface 114 in more than one plane with the axis of rotation of each of the rotation planes of the patient support surface 114 being parallel to and spaced from an axis that passes through the isocenter 124.

Simply rotating the couch 114 about an axis of rotation parallel to and spaced from an axis that passes through the isocenter 124 (also referred to herein as off isocenter rotation) from a first rotational position to a second rotational position would cause a portion of the couch 114 located at the isocenter 124 when the couch 114 is in its first rotational position to move away from the isocenter 124 when the couch 114 is in its second rotational position. In a treatment context, this would cause the target region of a patient 140 on the couch 114 to move away from the isocenter 124 when rotating the couch 114, which would result in an increased dosage of radiation being received by healthy tissue. Furthermore, this would result in a longer treatment time because the target region would not receive the intended dosage of radiation.

Accordingly, the subject support surface 114 is configured to move a particular section of the subject support surface 114 within a plane that is perpendicular to the axis of rotation separately from the rest of the subject support surface 114 and in such a way as to enable a portion of the couch 114 to be maintained substantially at the isocenter 124. In particular, the subject support surface comprises one or more sections 127, 128 which is/are configured to move from a first position to a second position along at least one of a longitudinal 113 and lateral 115 direction, or a direction oblique to these. These directions are referred to relative to the couch 114, regardless of the rotational orientation of the couch 114 at the time. The movement of this section of the couch 114 can be used to compensate for the relative displacement of a particular portion of the couch 114 away from the isocenter 124 that is caused by the off isocenter rotation of the couch 114. In particular, a section 127, 128 of the couch 114 can be moved in such a way as to maintain a particular portion of the subject support surface 114 substantially at the isocenter 124 whilst the couch 114 itself is rotated. The movement of the section 127, 128 of the couch 114 is controlled by a processor as a function of the rotation of subject support surface 114 so as to maintain the portion of the subject support surface 114 substantially at the isocenter 124.

For example, when a couch 114 is in a neutral rotational position (in which its longitudinal axis 113 is parallel to the fixed axis 119 (of the gantry 116 in its neutral position)), a portion of the couch 114 is located at the isocenter 124. When the couch 114 is rotated by the rotation mechanism 120 to a rotated position, for example of 10 degrees clockwise, this portion moves away from the isocenter 124. The apparatus also comprises a memory, which stores information such as the dimensions of the couch 114, different sections of the couch 126, 127, 128, the position of the isocenter 124, the dimensions of the gantry 116 and gantry cover, the location of the axis of rotation of the couch 114 and its position relative to the isocenter 124, and other useful information. The processor can use this information in a collision matrix to ensure that the system knows when and how collisions can appear and controls the movement and rotation of the couch 114 to avoid this. The processor can use such information to calculate the movement of the portion of a couch 114 that is or will be caused by a particular amount of rotation. The processor then calculates the amount of movement of the couch 114 in one or more of a longitudinal and lateral direction (relative to the couch 114 in its particular rotated position) that would be required in order to return (or maintain) the portion of the couch 114 back to the isocenter 124. The processor then controls the movement of a section 127, 128 of the couch 114 according to the calculated amount in such a way that the portion of the couch 114 is maintained (or returned) to the isocenter 124.

The processor can also be configured to control the rotation of the couch 114. The processor can be configured to calculate movement of the section 127, 128 that will be necessary or desired, before the rotation actually occurs. For example, the processor can plan the rotation of the couch 114 and corresponding movement of the section 127, 128 as part of a treatment plan. The rotation and the movement can therefore occur simultaneously to ensure that the portion of the couch 114 is maintained substantially at the isocenter 124 in a first rotational position in a second rotational position and in every rotational position between these positions. Alternatively, the rotation of the couch 114 can occur by manual operation (e.g. by an operator) and the processor can then calculate and command the necessary movement of a section 127, 128 of the couch 114 reactively, although, due to fast processing times, this may appear to an observer to be occurring in real time. The processor can be comprised within the couch 114 or can be located separately, for example, in a control room. The processor can also use information such as the dimensions and relative configuration of the gantry 116 to determine a maximum rotation angle possible for a particular couch 114 configuration without interference, and thereby ensure that the rotation does not result in the couch 114 contacting the gantry 116 in an unwanted manner.

The processor that controls the movement of the section 127, 128 may be the same processor as for the MR imaging apparatus 112 or RT apparatus and thus can also be configured to control the emission and rotation of the radiation source 106. In this way, the rotation of the couch 114 can be planned as part of a broader treatment plan and can be coordinated with the operation of the RT apparatus more generally in such a way as to optimise the treatment by reducing treatment times and minimising damage to healthy tissue.

Because the axis of rotation is parallel to and spaced from an axis that passes through the isocenter 124, it is not necessary to locate the rotation mechanism 120 within the plane of the radiation, as is shown in FIG. 1, in order to get the benefits of true isocentric rotation. Instead, it is possible to use a large variety of rotation mechanisms 120, such as those that are located outside of the plane of the gantry 116 and therefore the plane of radiation, or isoline. This is particularly useful for ring gantry/bore solutions or devices with 360° rotation of the gantry 116, for which it is problematic to position the rotation mechanism 120 within the radiation plane without interfering with the gantry 116. However, this disclosure is applicable to any radiotherapy device. Whilst the disclosure is not limited to bore solutions (ring gantries), bore solutions offer improved device stability. Furthermore, bore solutions are less imposing or alarming for patients. Bore solutions therefore may be desirable. The disclosure provides means to supply non-coplanar treatments (in which both gantry 116 and patient support surface 114 are rotated) in a radiotherapy device with a bore solution. Positioning the rotation means outside the plane of radiation also minimises radiation interference.

In this way, it is possible to maintain a portion of the couch 114 (and therefore a target region of a patient 140) substantially at the isocenter 124 whilst rotating the couch 114 (and patient 140) so that the radiation dose can be spread through the healthy tissue and meaning that the radiation dose received by healthy tissue surrounding a target region is minimised. This improves patient 140 wellbeing. The disclosure also provides an apparatus that utilises rotation means 120 which are located outside of the plane of the gantry 116 and therefore the plane of radiation, or isoline. Positioning the rotation means 120 outside the plane of radiation minimises radiation interference.

Examples of specific linkages and structures will now be described.

Figure 4:
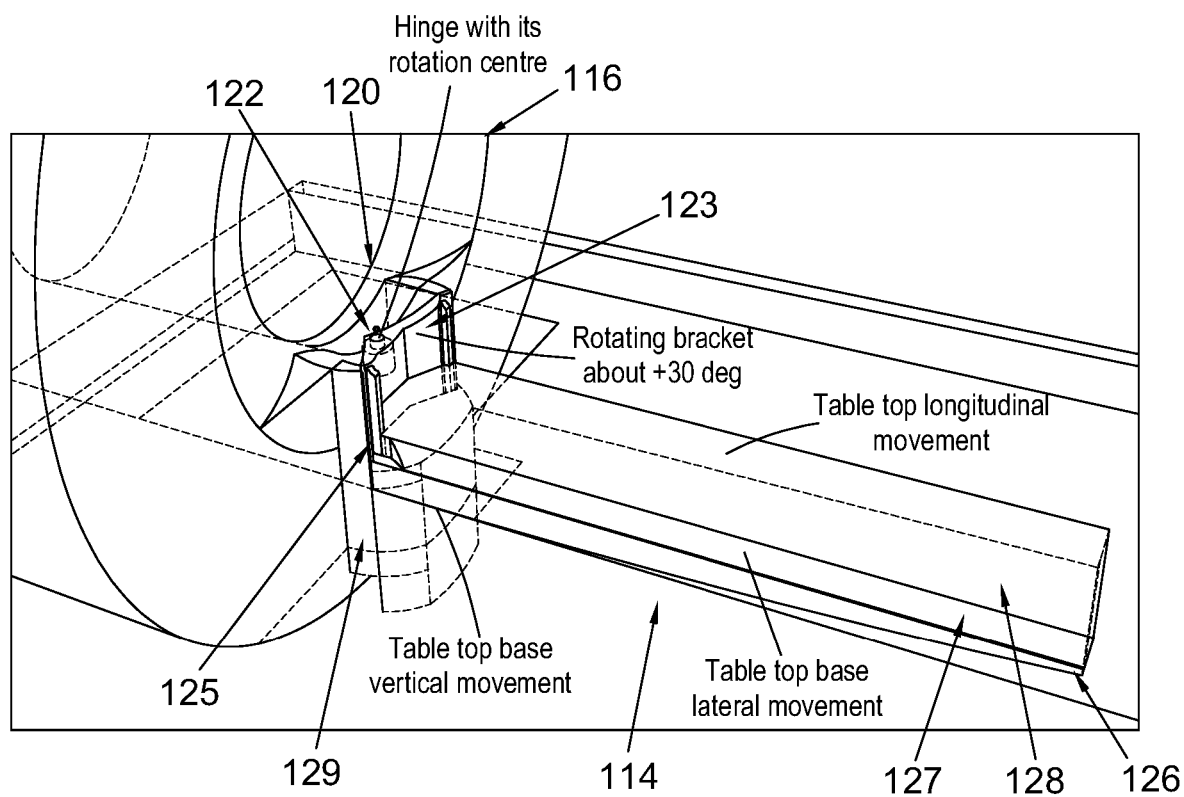
FIG. 4 depicts an isometric view of an embodiment of the radiotherapy device comprising a hinge about which the subject support surface is configured to rotate, wherein the subject support surface is in a lowered and non-extended position.
Figure 5:
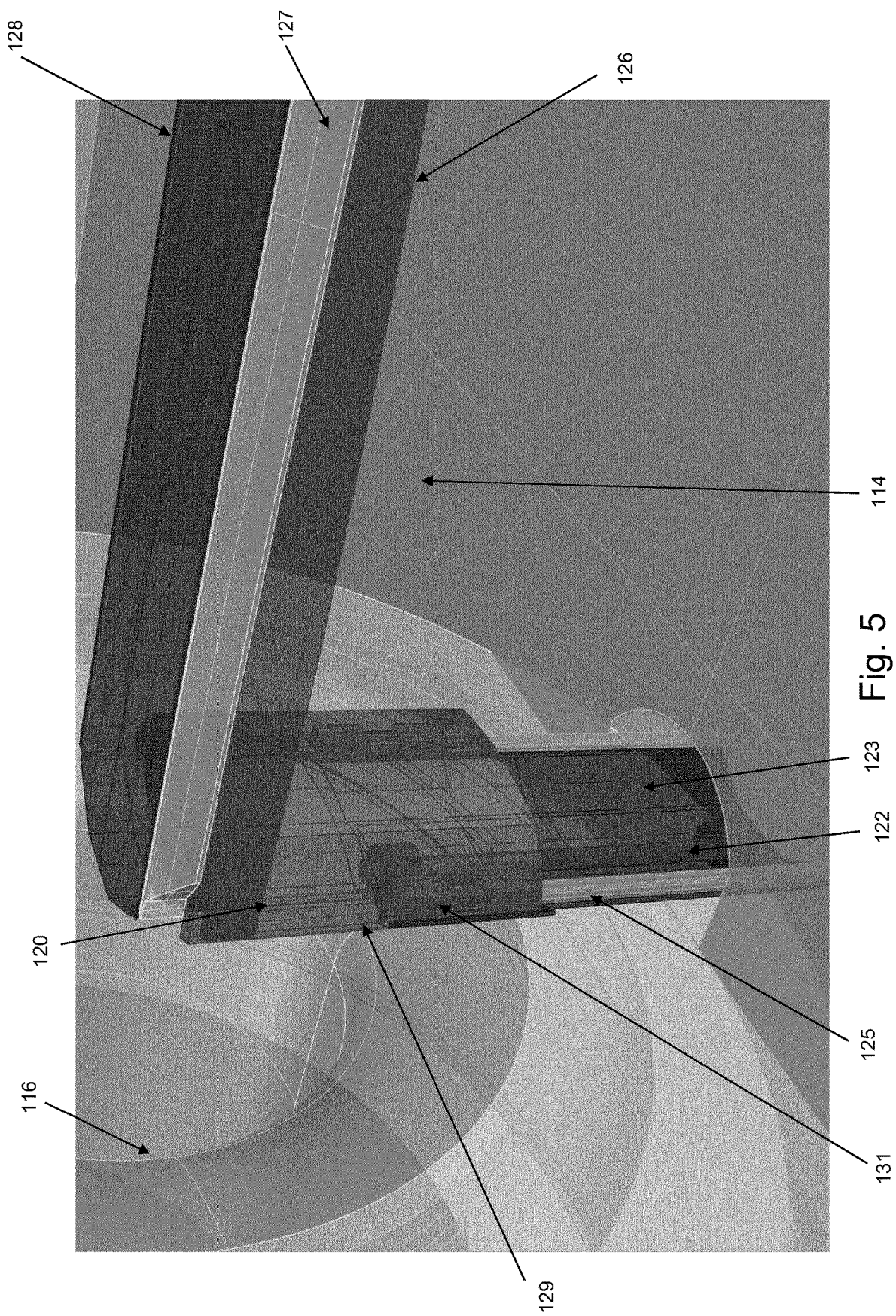
FIG. 5 depicts an isometric view of an embodiment of the radiotherapy device comprising a hinge, wherein the subject support surface is in a raised, non-rotated and non-extended position.

One embodiment is shown from different perspectives and in different positions in FIGS. 4, 5 6A, 6B and 7. These figures show a subject support surface 114 supported by and connected to a rotation mechanism 120. The rotation mechanism 120 comprises a rigid hinge 122 with the longitudinal axis of the hinge parallel to the vertical axis 111, a rotatable bracket 123 and two vertical sliders or guide rails 125. The rotatable bracket 123 is configured to rotate about the hinge 122 and therefore is configured to rotate about the vertical axis. The rotation of the hinge can be driven by one or more motors, such as electric motors, although in some examples it can also be rotated manually, for example by certain increments. The hinge 122 is attached directly to the gantry 116 (or gantry cover) and is fixed in relation to the gantry 116. The rotatable bracket 124 is rotatably connected to the hinge 122, for example, by a mechanical pivot, so that it is configured to rotate about an axis of rotation that passes through the longitudinal axis of the hinge 122. The hinge 122 is spaced from the isocenter 124 and therefore, by rotating about the hinge 122, the couch 114 is configured to rotate about an axis of rotation parallel to and spaced from an axis that passes through the isocenter 124. The whole rotation mechanism 120 is located outside the plane of the gantry 116 and outside the plane of radiation. The rotating bracket 123 is configured to hold the two guide rails 125, which are bolted on to the rotating bracket 123 as can be seen in FIG. 5. The couch 114 is connected directly to the rotation mechanism 120 or via an intermediary and can be connected by any suitable means, for example, mechanically. The rotation is controlled by a processor which may be comprised in the patient support surface 114 or may be located elsewhere. For example, the processor can control the speed of rotation or the angle of rotation of the couch 114.

The rotation mechanism 120 also comprises sliding covers 129 which cover the guide rails 125 to prevent anything becoming caught in the vertical motion mechanism and to prevent pinching hazards. The sliding covers 129 are configured to accommodate the rotation of the bracket 123. In one example, the sliding covers 129 are made of a flexible material such as rubber, that can accommodate this rotation.

Alternatively, the sliding covers 129 may be separate from the rotation mechanism but attached to the gantry 116 in such a way as to still protect the vertical guide rails 125 when the couch 114 is in both a non-rotated and rotated position.

The couch 114 comprises bottom section 126, a middle section 127 and a top section 128. The bottom section 126 is movably connected to the two vertical guide rails 125 in such a way that the bottom section 126 is configured to move from a first position to a second position along a vertical direction (along a vertical axis 111 that is an axis perpendicular to the floor). In one example, the bottom section 126 comprises carrier cars (guide rail cars) 131 that are configured to slide along linear guides (guide rails) 125 that are connected to the rotatable bracket 123. This movement is driven by one or more motors that can be located either on the rotatable bracket 123 or on the bottom section 126. The vertical direction 111 may also be described as the Z direction 111 or just vertically. For example, the bottom section 126 can be moved vertically from a lowered position (as shown in FIG. 4) to a raised position. The top section 128 is supported by the middle section 127, which is supported by the bottom section 126. Thus, when the bottom section 126 is raised or lowered, the middle and top sections 127, 128 are also raised or lowered. In this way, the whole of the couch 114 can be raised or lowered (moved vertically from a first position to a second position) along the vertical sliders of the rotation mechanism 120.

The middle section 127 (which may be described as a first or second section) is configured to move independently from the bottom section 126 in a lateral direction (along a transverse axis 113 of the patient support surface 114) from a first position to a second position. In one example, the middle section 127 is configured to move along guide rails and this movement can be powered by one or more electric motors and, for example, a ball screw, belt drive or other suitable means. The lateral or transverse direction 115 may be described as the X direction 115. The top section 128 is supported by the middle section 127 and, accordingly, when the middle section 127 is moved in a lateral direction 115, the top section 128 is also moved in a lateral direction with it. In one example, the middle section 127 is configured to move in a lateral direction when the bottom section 126 is in a raised position.

The top section 128 (which may be described as a first or second section) is configured to move independently from the bottom and middle sections 126, 127 in a longitudinal direction (along a longitudinal axis 113 of the patient support surface 114) from a first position to a second position. In one example, the top section 128 is configured to move along guide rails and this movement can be powered by one or more electric motors and, for example, a ball screw, belt drive or other suitable means. The longitudinal direction 113 may be described as Y direction 113.

In one example, the top section 128 and the middle section 127 are in fact the same section, and this combined section (which may be described as a first section) is configured to move independently from the bottom section 126 from a first position to a second position along at least one of a longitudinal 113 and lateral 115 direction or in a direction oblique to these.

A processor is configured to control the movement of the bottom, middle and top sections 126, 127, 128. In the present example, this processor is the same as the processor that controls the rotation of the couch 114.

As stated previously, the hinge 122 is spaced from the isocenter 124 and the rotatable bracket 123 and thus the couch 114 (which is connected to the bracket 123) are configured to rotate about the hinge 122. Thus, the couch 114 is configured to rotate about an axis of rotation parallel to and spaced from an axis that passes through the isocenter 124. As explained previously, this results in a portion of the couch 114 that is located at the isocenter in the non-rotated position of the couch 114, moving away from the isocenter 124 when the couch 114 is rotated. The apparatus also comprises a memory in which it can store information such as the dimensions of the different sections 126,127,128 of the couch 114, the position of the hinge 122 relative to the isocenter 124, the dimensions of the gantry 116 and gantry cover and other information useful to performing a treatment. The processor uses information such as this to calculate how much the previously mentioned portion of the couch 114 will have moved for a particular rotation angle of the couch 114. The processor then calculates how much lateral and/or longitudinal movement is needed in order to maintain the portion of the couch 114 at the isocenter 124 for the rotation angle. In this example, the processor then executes commands causing the couch 114 to rotate to the particular angle, the middle section 127 to move by the needed lateral amount, and the top section 128 to move by the needed longitudinal amount.

In this example, the processor is also used to control the rotation and emission of the radiation and could also be used to control other operation of the radiotherapy device. This allow the rotation of the couch 114 to be synchronized with the operation of the radiotherapy device or delivery of the radiotherapy treatment. One example of a treatment shall now be described.

The couch 114 starts in a lowered and neutral position (the bottom section 126 is lowered, the middle and top sections 127, 128 are not extended, and the couch 114 is not rotated), as illustrated in FIG. 4. A patient 140 then lies on the couch 114 on top of the top section 128, which is made easy for the patient 140 by virtue of the couch 114 being lower to the ground. An operator then starts the treatment, for example, by pressing a start button. The operator may also input a number of treatment parameters in a computer, which can then be used by the processor to control the treatment. First the bottom section 126 is raised (thereby raising the couch 114 and the patient 140), as illustrated in FIG. 5. The movement of the bottom section 126 is controlled by one or more guide rail cars 131, which are configured to move up and down the guide rails 125, which are bolted to the rotatable bracket 123. FIG. 5 depicts the subject support surface 114 in a raised, non-extended and non-rotated position.

Figure 6A:
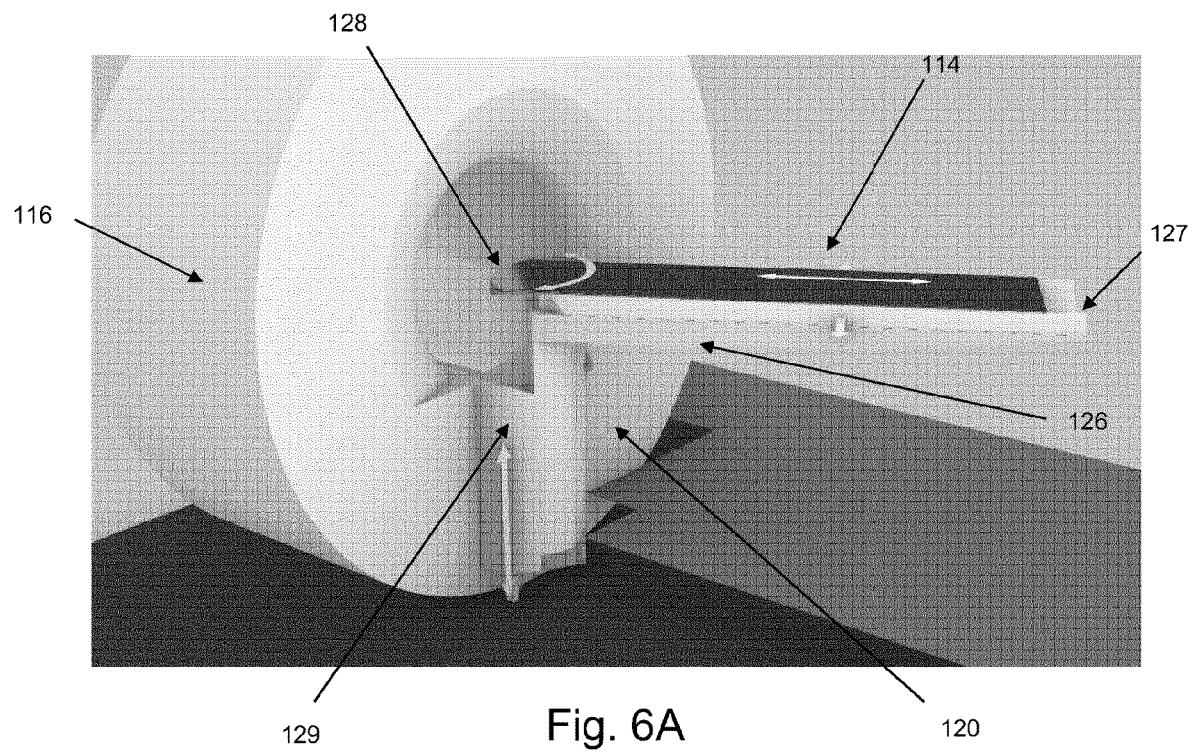
FIG. 6A depicts an isometric view of an embodiment of the radiotherapy device comprising a hinge, wherein the subject support surface is in a raised, rotated and non-extended position.
Figure 6B:
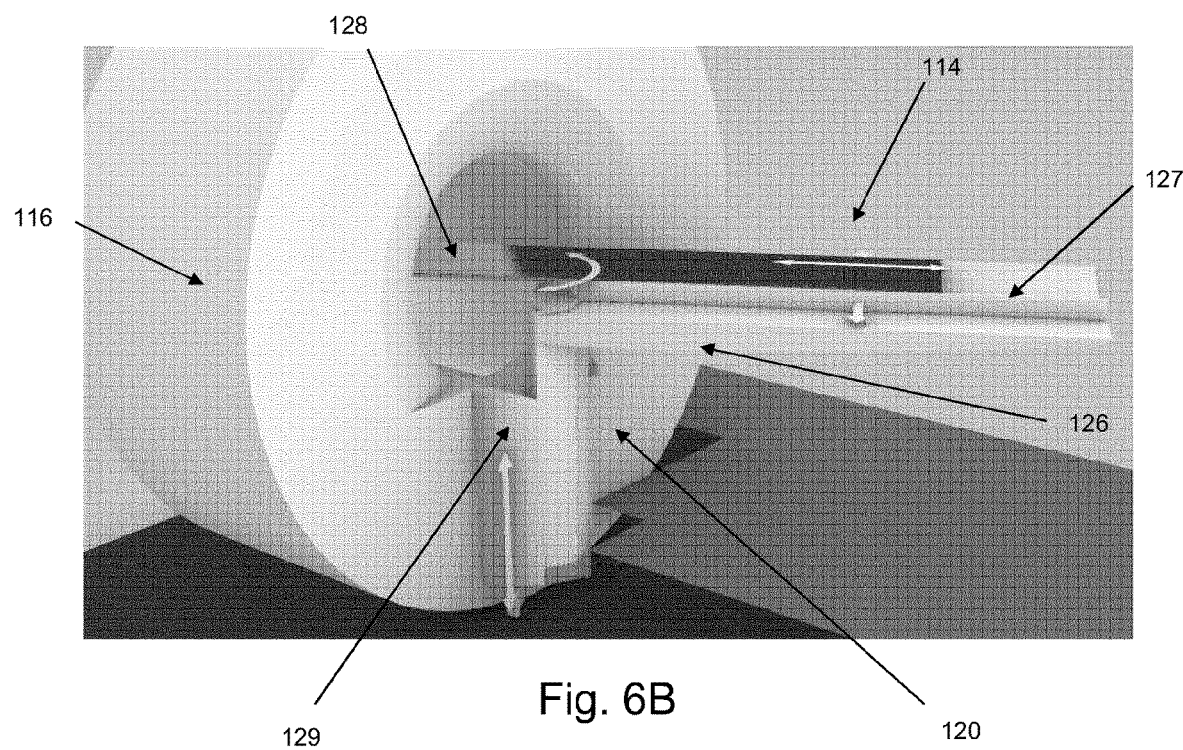
FIG. 6B depicts an isometric view of an embodiment of the radiotherapy device comprising a hinge, wherein the subject support surface is in a raised, rotated and extended position and wherein the middle section has moved laterally in order to maintain a portion of the subject support surface substantially at the isocenter.

Once the couch 114 has been raised, the top section 128 with the patient 140 on it is extended into a bore of the gantry and into the plane of radiation. Alternatively, the couch 114 may be rotated without extending the top section 128 first, as illustrated in FIG. 6A. Then, after the couch 114 has been rotated, the top section 128 can then be extended as shown in FIG. 6B. The approximate position of a target region of the patient 140 is known prior to the treatment and so it can estimated by the operator or processor how far to extend the patient 140 into the bore so as to position the target region approximately at the same point as the isocenter 124. This initial positioning (which includes the amount of vertical and longitudinal movement of the couch) can be performed by an operator using a control pad connected to the couch 114 or located remotely, and may be assisted by the use of lasers or markers on the patient's body. In one example, where the target region is on one side of the patient's body, the movement of the middle section 127 in a lateral direction can also be controlled at this stage to position the target region in the desired position.

In one example, the patient 140 is then scanned using the MR imaging apparatus 112 which allows the exact position of the target region, for example a tumour, to be determined. The operator or processor can then make any necessary small adjustments to the positioning of the different sections of the couch 114 according to the determined location of the target region in situ, so that the target region can be precisely located at the isocenter 124 or other desired location. When the couch 114 (and therefore the patient 140) is in the correct starting position for the treatment, this position is recorded by the operator indicating that it is in the correct position, and the processor then stores this position and the relative positions of all of the sections in the processor memory as the start position.

Figure 7:
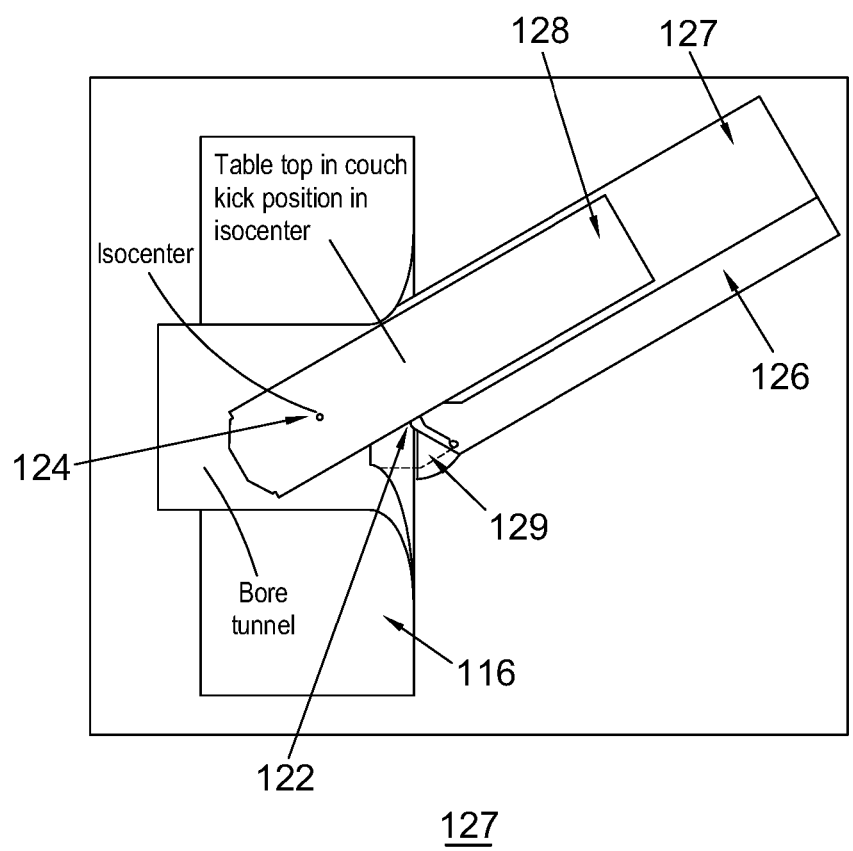
FIG. 7 depicts a plan view of an embodiment of the radiotherapy device comprising a hinge, wherein the subject support surface is in a rotated, raised and extended position.

The processor can then control the radiotherapy device by controlling the source of radiation 106 in such a way as to emit a treatment beam 110 and by rotating the gantry 116 so as to rotate the source of radiation 106 about the isocenter 124, thus exposing the target region to a desired amount of radiation from a range of different angles, as is known in the art. In this example, once the patient 140 has been exposed to a desired level of radiation from the angles in the current plane of radiation, the source of radiation 106 is then temporarily stopped. In one example, the processor then instructs the rotation mechanism 120 to rotate from the first neutral position to a second rotated position, for example 10 degrees clockwise, which results in the couch 114 rotating to an angle of 10 degrees clockwise to a couch kick position. FIG. 6B and FIG. 7 illustrates the couch 114 in its raised, rotated and extended position. It should be noted that the rotation and the extension can occur one after another, in either order, or at the same time. At the same time, the processor is configured to instruct the middle and top sections 127, 128 to extend laterally and/or longitudinally by the amount that is required in order to maintain the target region substantially at the isocenter 124, whilst the couch 114 is in the rotated position. The rotation and the movement of the different sections 127, 128 are executed simultaneously and in one example, are controlled at a speed that results in the same time for completion of each of the sections' movements and for the rotation, so that the patient 140 is moved smoothly into the rotated position, with minimal juddering that would be caused by the rotation and the sections moving sequentially. This maximises patient comfort 140 during the rotation.

Once the couch 114 is in its rotated and adjusted position, the processor instructs then controls the radiotherapy device in a similar manner to that described previously. The plane of radiation will then pass through a different part of the patient's body, except for at the isocenter 124, at which the target region is located, which will be exposed to a second dose of radiation. Again, once the patient 140 or target region has been exposed to a desired amount of radiation, the radiation is stopped. The couch 114 can then be rotated to another angle with the sections 127, 128 compensating for this rotation as described previously, and the process then repeated. This can be done for any number of different rotation angles (although in this example, limited by obstruction of the gantry cover to an angle of 30 degrees clockwise and anticlockwise of neutral). As described above, the treatment starts in the neutral position and then moves 10 degrees clockwise, which may then be followed by 20 and 30 degrees clockwise before 10, 20 and 30 degrees anticlockwise (taken from neutral), thus resulting in a total of 7 doses of radiation at 7 different angles. Alternatively, the treatment could start by rotating the couch 114 to the maximum rotation angle in one direction and then only moving in one direction until the treatment was ready to finish. Many other such treatment plans are also possible.

Once the patient 140 has been exposed to the desired level of radiation from all the desired angles, the rotation mechanism 120 returns to its neutral, non-rotated, position, the sections 127, 128 return to their neutral (retracted/non-extended) positions and the couch 114 is then vertically lowered, to enable the patient 140 to easily dismount. Being able to start with the couch 114 in a lowered position enables a low get on/get off height for the patient 140, which can be an advantage for less mobile (for example overweight) patients 140.

The couch 114 can be made out of many different materials. In one example, the table top 128 is made of or comprises a composite, such as carbon fibre or similar strength fibre such as Kevlar. The rotatable bracket 123, the hinge 122, the bottom section 126 and the middle section 127 can be made of a metal, such as steel, cast iron or aluminium or another appropriate material. In one example, the rotatable bracket 123 and the hinge 122 are made of steel, the bottom section 126 is made of steel or cast aluminium and the middle section 127 is made of aluminium, which could be cast, milled or a combination.

By mounting the rotation mechanism 120 directly to the gantry 116, it enables the apparatus to be pre-aligned in a factory during manufacture. It also maintains an open floor area underneath the couch 114 which, for example, enables a patient 140 to more easily mount the couch 114. It does not need extra space around the couch and therefore does not interfere with the radiotherapist (operator) during patient 140 positioning. Furthermore, this apparatus provides a couch kick (rotatable couch 114) with a regular size of top and base. There is therefore no bulky construction to obstruct the radiotherapist.

As described in the embodiment above, the couch 114 comprises three different sections 126, 127, 128 all of which are responsible for a different axis of movement. However, it is also possible for the top and middle sections 128, 127 to in fact only be one upper section that is configured to move in both directions, or at an angle oblique to these, as shall be described in more detail with reference to other embodiments.

The rotation of the patient support system 114 can occur before, during or after treatment. Rotation can be continuous or discrete/static. Rotation of the couch 114 may also occur with the top section 128 extended or not extended. Movement of the different sections 126, 127, 128 of the couch 114 can occur at the same time as each other and as the rotation of the couch 114, or separately, sequentially. The speeds of the movement(s) can be controlled so that the time for a particular movement is the same as the time of a corresponding rotation at a particular speed. One or more of the movements of the sections 126, 127, 128 or the rotation of the rotation mechanism 120 can also be controlled manually by the operator, with the processor calculating and compensating for such a movement.

The couch 114 may include a number of rollers or other parts as well as the sections 126, 127, 128. In these figures, the rotation mechanism 120 is connected directly to the gantry 116 but it could be connected to a floor, a wall or other support structure instead or as well. For example, when referring to the portion of the couch 114 being maintained substantially at the isocenter 124, this could be actually at the isocenter 124 or within 0.005 to 0.015 mm, more preferably 0.01 mm, 0.05 mm to 0.15 mm, more preferably 0.1 mm, 0.15 mm to 0.25 mm, more preferably 0.2 mm, 0.25 to 0.35 mm, more preferably 0.3 mm, 0.35 mm to 0.45 mm, more preferably 0.4 mm, 0.45 mm to 0.55 mm, more preferably 0.5 mm, 0.5 mm to 1.5 mm, more preferably 1 mm, or another distance of the isocenter 124.

Another embodiment is illustrated in FIGS. 8, 9A, 9B, 9C, 10A and 10B. These show a patient support surface 114 supported by and connected to a rotation mechanism 120. The rotation mechanism 120 comprises a swivel arm 130. The swivel arm 130 has two rotation axis and comprises first and second points of rotation 132, 134. The swivel arm 130 is connected to the floor towards the end of the swivel arm 130 closest to the radiotherapy device at the first point of rotation 132. The swivel arm 130 can be connected directly to the floor at the first point of rotation 132, or via an intermediary, such as a cog-wheel, and can be connected by any suitable means, for example, by a mechanical pivot. In one example, at the first point of rotation 132, the swivel arm 130 is connected to the floor by a first cog-wheel rigidly connected to the floor. The swivel arm 130 is pivotally connected to the first cog-wheel. The swivel arm 130 is configured to rotate around the centre of the first cog-wheel, which is located at the first point of rotation 132. The first cog-wheel is located underneath the swivel arm 130 (in other words, between the swivel arm 130 and the floor) but could instead be located above the swivel arm 130.

The swivel arm 130 is connected towards the end further from the radiotherapy device, to the couch 114 at the second point of rotation 134. The couch 114 can be connected directly to the swivel arm 130 at the second point of rotation 134, or via an intermediary, such as a cog-wheel, and can be connected by any suitable means, for example, by a mechanical pivot. In one example, at the second point of rotation 134, the swivel arm 130 is connected to the couch 114 by a second cog-wheel rigidly connected to the upper part of the couch 114. The swivel arm 130 is pivotally connected to the second cog-wheel. The second cog-wheel and the couch 114 are rigidly connected and do not rotate relative to one another but are both configured to rotate together about the second point of rotation 134 and relative to the swivel arm 130. The second cog-wheel is located underneath the swivel arm 130 (in other words, between the swivel arm 130 and the floor) but could instead be located above the swivel arm 130.

The swivel arm 130, first and second points of rotation 132, 134 are all located outside of the plane of the gantry 116 and the plane of radiation. Accordingly, the rotation mechanism 120 is located outside the plane of the gantry 116 and outside the plane of radiation.

Figures 9A, 9B:
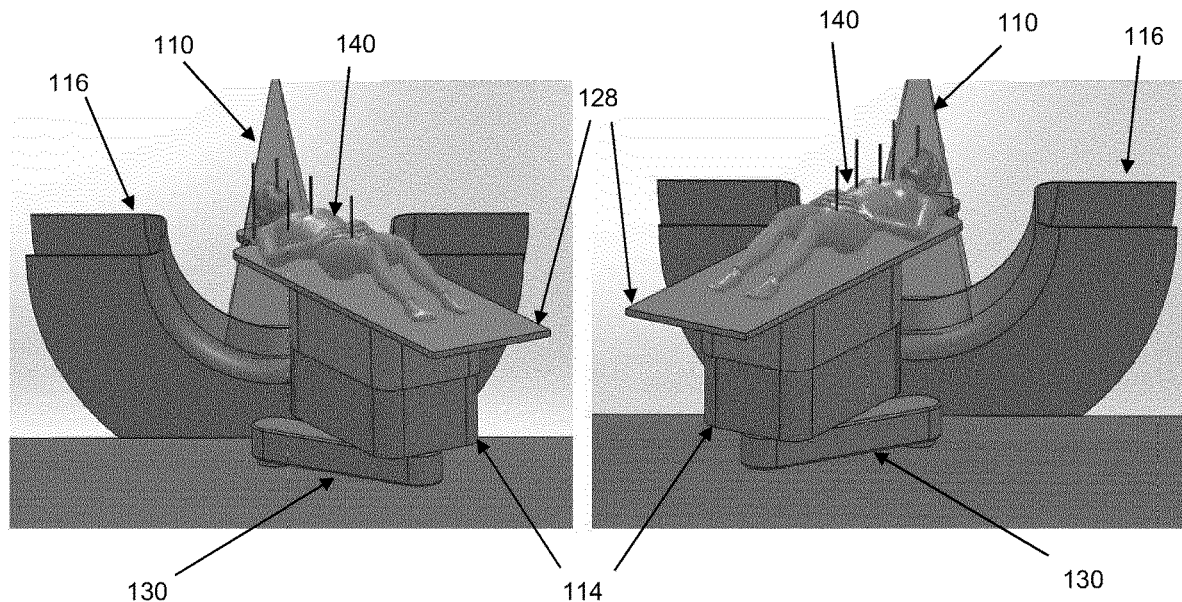
FIG. 9A depicts an isometric view of an embodiment of the radiotherapy device with a rotation mechanism comprising a swivel arm with the subject support surface in a raised and rotated position.
FIG. 9B depicts an isometric view of an embodiment of the radiotherapy device with a rotation mechanism comprising a swivel arm with the subject support surface in a raised and rotated position.
Figure 9C:
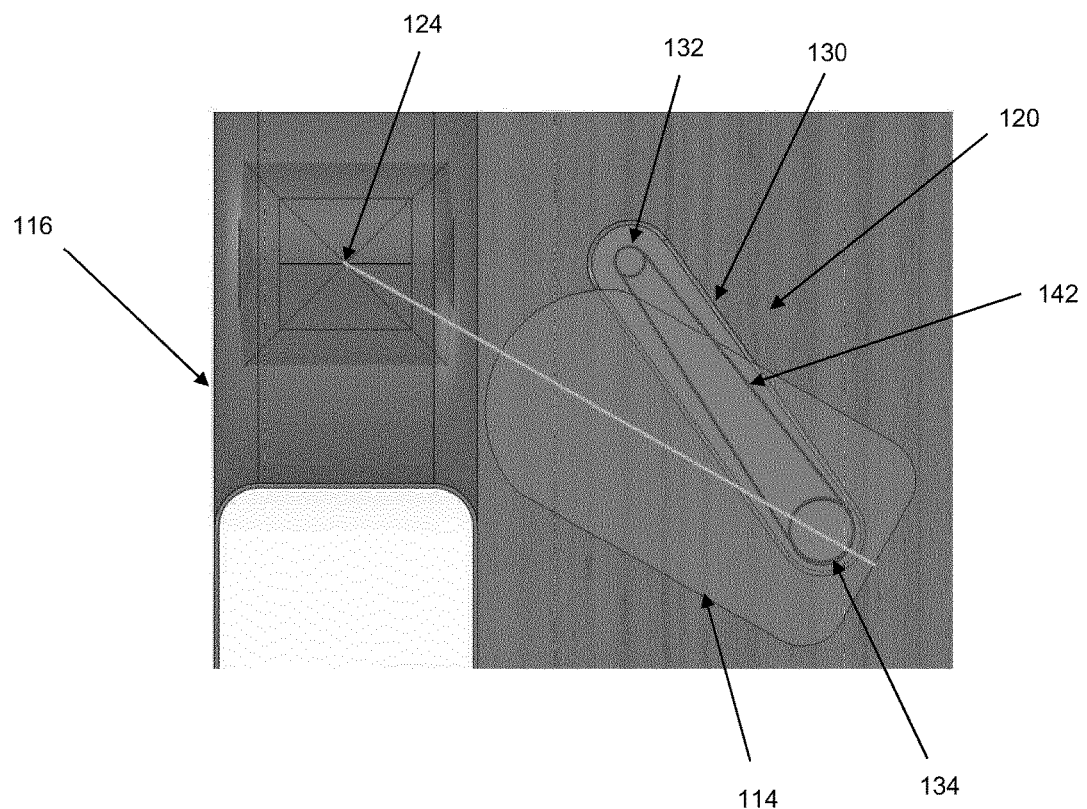
FIG. 9C depicts a plan view of an embodiment of the radiotherapy device with a rotation mechanism comprising a swivel arm with the subject support surface in a rotated position.

The swivel arm 130 may comprise a belt, chain wheel, cog or other suitable feature located at the first and second points of rotation 132, 134. The first and second rotation points 132, 134 and the features located at these points may be connected by a connecting belt or chain 142, as shown in FIG. 9C. The length of the swivel arm 130 (as given by the distance between the centres of the points of rotation) is half the distance between the isocenter 124 and the second rotation point 134. The two rotation points are connected with a gear ratio of 1:2 between the first and second rotation points 132, 134 respectively. This is achieved by a variety of suitable means, for example the use of cog-wheels located at the rotation points, as described above. In one example, at each of the first and second rotation points 132, 134, there is a steel shaft, two (angular-contact) bearings and a chain or cogged belt wheel. The connection between the two rotation points 132, 134 may be a chain or cogged belt.

The two cog-wheels, chain wheels or other features located at the rotation points act as transmission components, which facilitate a co-ordinated rotation of the swivel arm 130 with respect to the floor and the couch 114 with respect to the swivel arm 130. For example, a first wheel is rigidly connected to the floor at the first rotation point 132 and a second wheel is rigidly connected to the couch 114 at the second rotation point 134. The swivel arm 130 is pivotally connected to the first wheel and to the second wheel. In one mode of operation, the couch is rotated by the application of an external force (for example it is pushed manually by an operator). With the wheels serving as transmission points for the rotation, the rotation mechanism 120 enables the couch 114 to automatically rotate about an axis that is parallel to and spaced from an axis that passes through the isocenter 124, without even needing a motor to drive the rotation.

Alternatively, the rotation of the chain wheels can be driven by one or more motors in such a way that, when the first wheel, located at the first point of rotation 132 is rotated, the second wheel, located at the second point of rotation 134 rotates at half the speed. This, together with the distances identified above, causes the couch 114 to rotate about an axis that is parallel to and spaced from an axis that passes through the isocenter 124 in such a way that the longitudinal axis of the couch 114 always points towards the isocenter 124, as illustrated in FIGS. 9A, 9B and 9C.

It is apparent that there are other examples of configurations that would result in a similar rotation of the couch 114. For example, if the first cog-wheel is rigidly connected to the swivel arm 130 and pivotally connected to the floor or the second cog-wheel is rigidly connected to the swivel arm 130 and pivotally connected to the couch 114.

Figure 8:
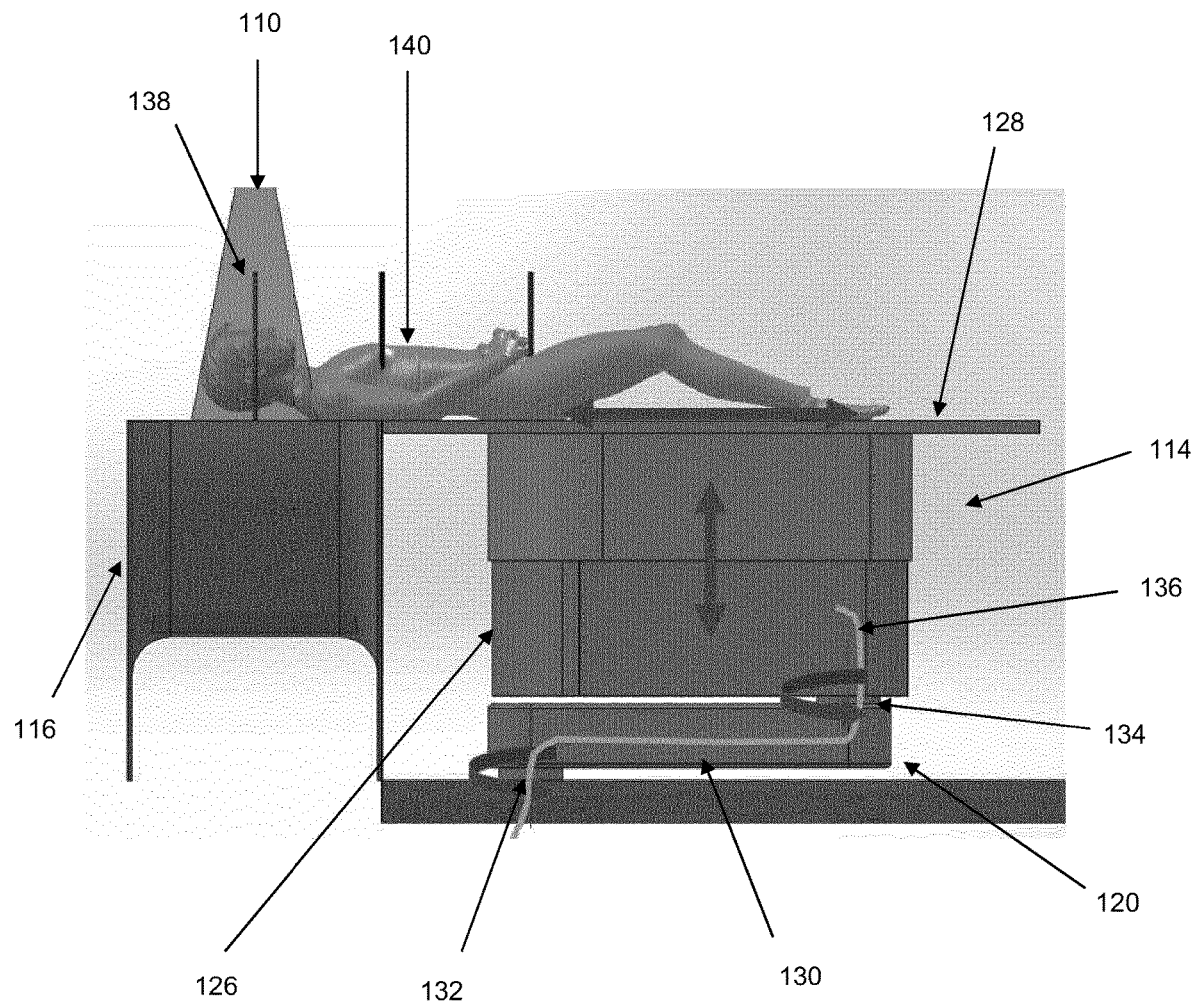
FIG. 8 depicts a side elevation view of an embodiment of the radiotherapy device with a rotation mechanism comprising a swivel arm.
Figure 10A:
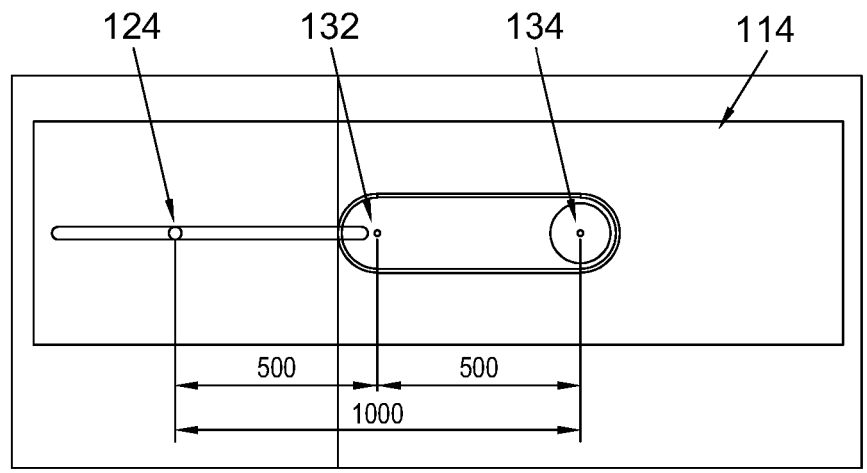
FIG. 10A depicts a plan view of an embodiment of the radiotherapy device with a rotation mechanism comprising a swivel arm with the subject support surface in a non-rotated position.
Figure 10B:
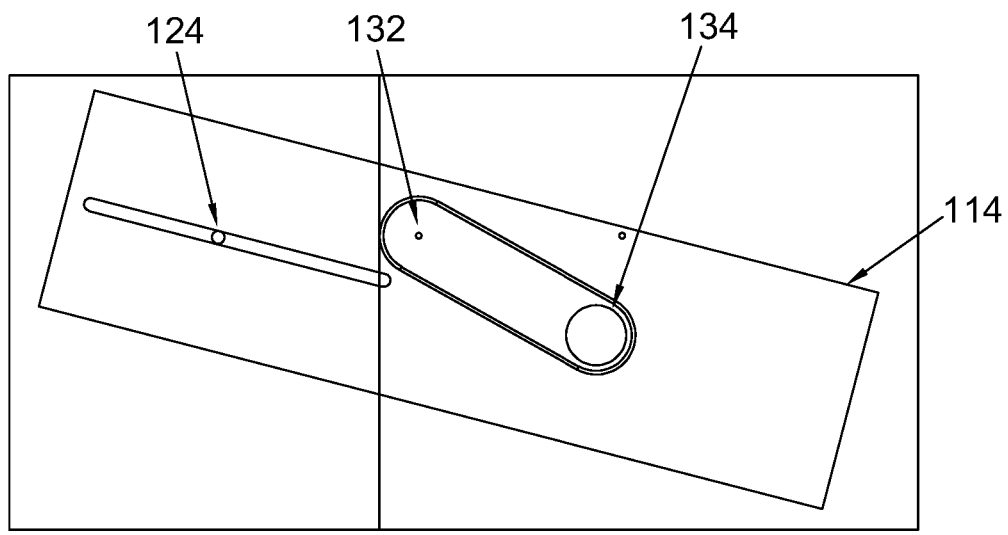
FIG. 10B depicts a plan view of an embodiment of the radiotherapy device with a rotation mechanism comprising a swivel arm with the subject support surface in a rotated position and illustrates the longitudinal movement of the couch that is caused by the rotation.

The patient support system 114 may include a number of rollers, a top (or upper) section 128, a bottom section 126, or other parts. As illustrated in FIG. 8, the couch 114 can extend vertically and/or longitudinally to enable optimised positioning of the patient 140 under the treatment beam 110, by maintaining a portion of the subject support surface 114 substantially at the isocenter 124. When the couch 114 is rotated, the position of the couch 114 relative to the isocenter 124 varies for a given rotation angle, as described previously. This is illustrated in FIGS. 10A and 10B which show the isocenter 124 located at a different part of the couch 114 for the two different rotation angles shown. Accordingly, the couch 114 (or a portion thereof in the form of a top section 128) is extended along the longitudinal axis 113 of the couch 114 in its rotated position, to compensate for this change of distance. This extension can be performed manually or can be controlled by a processor, such as a processor that also controls the rotation of the couch 114. The extension of the couch 114 or portion thereof can therefore be synchronised with the rotation of the couch 114 in such a way as to maintain optimised positioning of the patient 140 under the treatment beam 110.

Furthermore, the couch 114 or top section 128 can be rotated around the axis of the bore (rolled), and/or pivoted, as well as extended. In this way, it is possible to achieve six axis degree of freedom with regard to positioning a patient 140. In order for the couch 114 to extend the top section 128, electrical power can be supplied to the couch 114 via a cable 136 running from a power source and through the swivel arm 130. It is also possible for other cables to be passed through the swivel arm 130, for example, for sending control signals to the couch 114.

The first rotation point 132 of the swivel arm 130 is located at a position along the axis of the bore 119. When the swivel arm 130 is parallel to the axis of the bore, the second rotation point is also located at a position along the axis of the bore 119. Accordingly, in the neutral position of the couch 114, the isocenter 124 and the first and second points of rotation (132, 134) are all aligned, as illustrated in FIG. 10A. FIG. 10B shows the axis 113 of the longitudinal centreline of the couch 114 passing through the isocenter 124 when the couch 114 is in a rotated position. This rotation is caused automatically due to the configuration of the rotation mechanism 120, as described above.

The rotation of the patient positioning system 114 can occur before, during or after treatment. Rotation can be continuous or discrete/static. Rotation of the couch 114 may also occur with the top section 128 extended or not extended. Rotation of the couch 114 can also occur at the same time as top section 128 is being extended. In one example, a patient 140 lies on the couch 114 in its non-extended position. The couch 114 is then extended, the patient 140 is scanned and exposed to radiation. The radiation is then stopped, the couch 114 is rotated (yawed) by rotating the swivel arm 130 about the first and second rotation points 132, 134 as shown in FIGS. 9A and 9B and the patient 140 is then exposed to further radiation. In another example, the radiation is not stopped and the rotation of the couch 114 happens automatically and at the same time as the patient 140 is exposed to radiation.

The rotation about the first point of rotation 132 may be clockwise or anticlockwise. The rotation of the second point of rotation 134 is in the opposite direction to that of the first rotation point 132. It should be understood that when talking about the first and second points of rotation 132, 134, reference may be made to whatever physical entity is located at the point of rotation, such as an axle, motor or cog. The speed of rotation at the second point of rotation 134 is half that at the first point of rotation 132. This rotation may be caused by any appropriate means. For example, rotation of the first point of rotation 132 can be caused by a motor. The speed of the rotation at the first point of rotation 132 may be controller by a processor, which may be comprised in the patient support surface 114 or may be found elsewhere, for example in a control room. The rotation at the second point of rotation 134 may then be caused by a mechanical or physical connection with the first point of rotation 132.

Alternatively, the speed of rotation at both points of rotation 132, 134 may be controlled by the processor. For example, the processor might send a signal to a motor configured to cause rotation of the swivel arm 130 at the first point of rotation 132 and instruct the motor to cause rotation at a speed of 1 revolution per minute. The processor may also send a signal to a different motor configured to cause rotation of the swivel arm 130 at the second point of rotation 134 to cause rotation of the couch 114 on top of the swivel arm 130 at a speed of 2 revolutions per minute. These speeds are only examples and other speeds are possible. The speed of rotation should not be so great as to cause patient 140 discomfort but not slow as to be inefficient and increase treatment times. The placement of the motor, if used, is not essential for the function of the apparatus. There could be one or more motors located at any of the first rotation point 132, the second rotation point 134 or even somewhere in between the rotation points acting directly on the belt or chain connecting these rotation points. Alternatively, as described above, there may not be any motor and the couch 114 is rotated manually, whilst using the configuration of the apparatus to achieve the particular rotation of the couch 114.

The same processor may also be used to control the radiation emission or other operation of the radiotherapy device. This allows the rotation of the couch 114 to be synchronized with the delivery of the radiotherapy treatment. Alternatively, the operation of the radiotherapy device and the radiotherapy treatment may be controlled by a different, separate processor.

When installing the rotation mechanism 120 and the couch 114, the position of the couch 114 may be calibrated before use. This can be done by, for example, positioning the couch 114 in a neutral position with the longitudinal axis 113 of the couch 114 in its neutral position parallel to the longitudinal axis of the swivel arm 130. This may be set as 0° of rotation and the subsequent rotation of the couch 114 can be measured about this position. The neutral position is when the longitudinal axis 113 of the couch 114 is aligned with the axis of the bore of the gantry 116 (which may be perpendicular to the radiation plane in some configurations, and parallel to the floor (as shown in FIG. 10A). When the patient support system 114 is fully extended into the bore, there may be less rotation possible compared to when the patient support system 114 is not extended, or only partially extended, into the bore. As a result, this system is particularly well suited to treatments for head and neck.

The swivel arm 130 can by made from one or more different materials, for example, steel such as a welded steel sheet metal structure, cast iron, aluminium, titanium, composite, or any other material with high rigidity that is suitable to support the required loads.

Another embodiment is illustrated in FIGS. 11A and 11B. These show a patient support surface 114 supported by and connected to a rotation mechanism 120. The rotation mechanism 120 comprises a first sliding base 150 located on a first side of the gantry 116, a second sliding base 152 located on a second side of the gantry 116, a first support member 154, a second support member 156 and a third support member 158. The first sliding base 150 is connected to and supports the first support member 154 and the second support member 156. The second sliding base 152 is connected to and supports the third support member 158. The couch 114 is connected to and supported by the first and second support members 154, 156 at the proximal end of the couch 114. The couch 114 is connected to and supported by the third support member 158 at the distal end of the couch 114. The section of the couch 114 that is connected to the first, second and third support members 154, 156, 158 may also be referred to as a bridge or bottom section.

The first sliding base 150 in one example is mounted directly to the gantry 116 or a portion of the gantry, which protrudes 200-300 mm underneath the level of the floor so that the first sliding base 150 is mounted on the part of the gantry 116 that is underneath the floor. The first sliding base 150 is configured to move from a first position to a second position in a lateral direction along a guide rail mounted to the portion of the gantry 116 beneath the floor. Alternatively, the first sliding base 150 is supported by the floor itself and is configured to move from a first position to a second position in a lateral direction 113 along the floor. Similarly, the second sliding base 152 in one example is mounted directly to the gantry 116 or a portion of the gantry, which protrudes 200-300 mm underneath the level of the floor so that the second sliding base 152 is mounted on the part of the gantry 116 that is underneath the floor. The second sliding base 152 is configured to move from a first position to a second position in a lateral direction along a guide rail mounted to the portion of the gantry 116 beneath the floor. Alternatively, the second sliding base 152 is supported by the floor itself and is also configured to move from a first position to a second position in a lateral direction 113 along the floor. In one example, the first and second sliding bases 150, 152 are guided during this lateral movement by guide rails that are set into the floor and supported by the portion of the gantry that is beneath the floor. In another example, the first and second sliding bases 150, 152 are guided by first and second elongated slots in the floor, along which the sliding bases 150, 152 are configured to slide. The longitudinal axis of the elongated slots is aligned with the lateral axis 113 of the couch 114 in its neutral position (neutral lateral axis 113), which means that the sliding bases 150, 152 are configured to slide, parallel to each other, along a neutral lateral axis 113. For example, the first and second sliding bases 150, 152 move along linear movement guide rails and are driven by motors controlled by a processor and/or operated with, for example, one or more buttons.

The first and second support members 154, 156, which are both connected to the first sliding base 150, are both aligned along the neutral lateral axis 113 and are spaced apart from one another but both equidistant from the centre point of the first sliding base 150. The third support member 158 is connected to the second sliding base 152 and is located at the centre point of the second sliding base 152.

Figure 12:
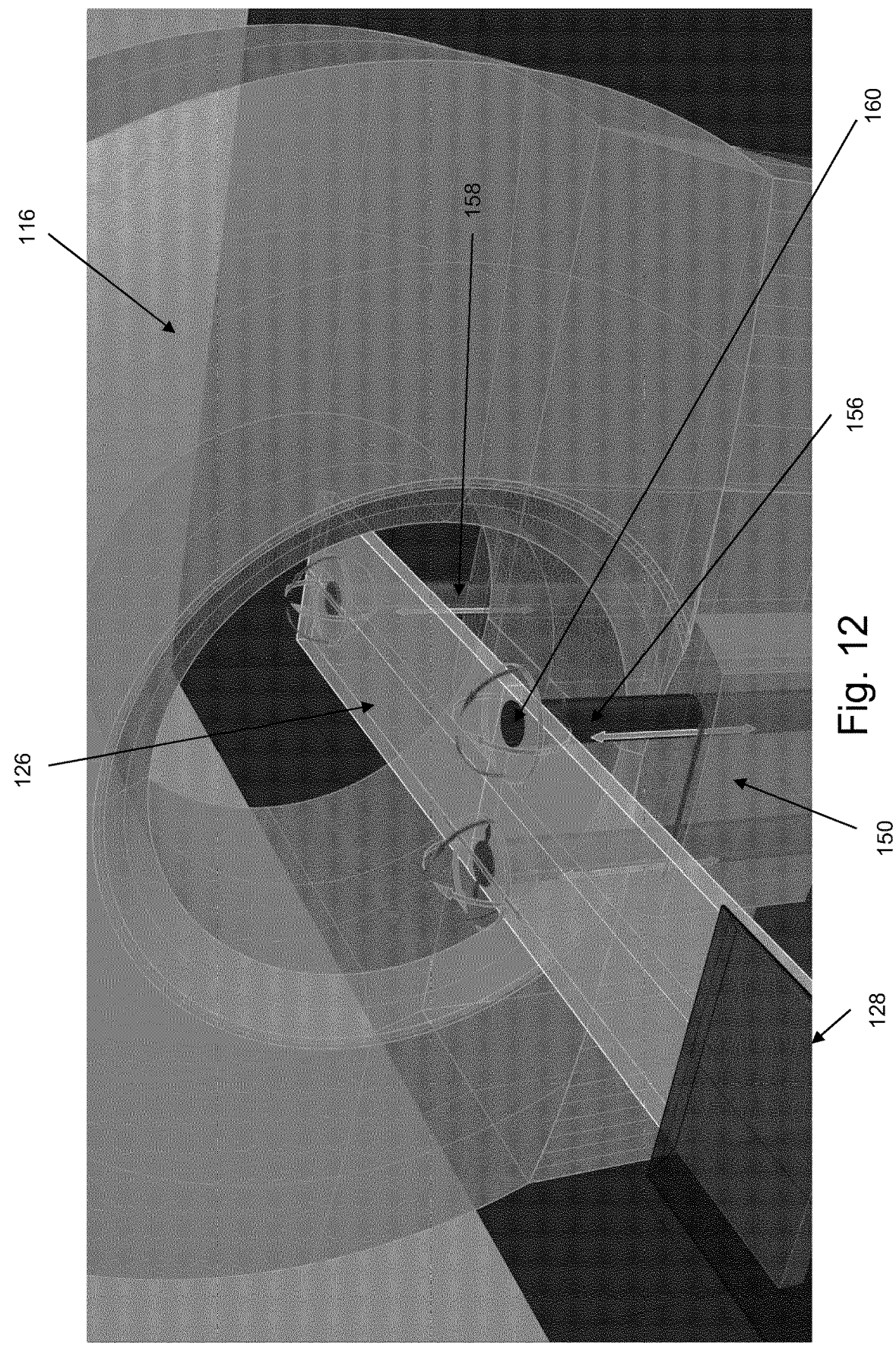
FIG. 12 depicts an isometric view of an embodiment of the radiotherapy device with a rotation mechanism comprising first and second sliding bases, wherein the subject support surface is in a non-rotated position.

The couch 114 comprises a bottom section 126 (bridge) and a top section 128, which is supported by the bottom section 126. The bottom section 126 is connected to the rotation mechanism 120 at three points. The second support member 156 is rotatably connected to the bottom section 126 at connection point 160. For example, this connection can be a ball and socket joint, as shown in FIG. 12, with the ball comprised as part of the second support member 156 and the socket comprised in the bottom section 126 of the couch 114 or vice versa. In this way, the bottom section 126 may be rotated about an axis of rotation that passes through the second support member 156 and the connection point 160.

Figure 13A:
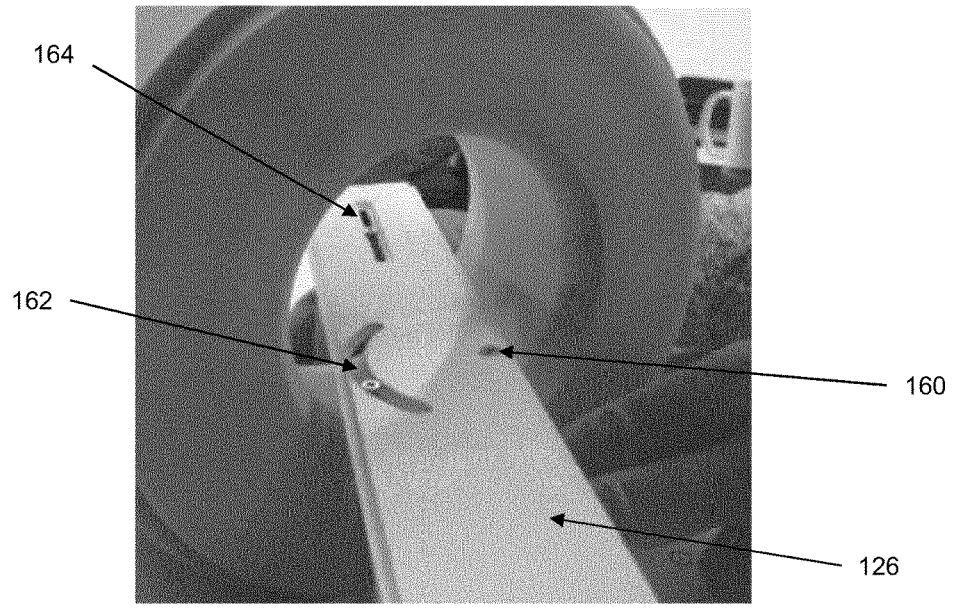
FIG. 13A depicts an isometric view of an embodiment of the radiotherapy device with a rotation mechanism comprising first and second sliding bases without the top section shown.

In order to enable such a rotation, the first support member 154 is movably connected to the bottom section 126 at a point that varies as the bottom section 126 is rotated about the second support member 156. To enable this point of connection to the bottom section 126 to move, the bottom section 126 comprises a curved slot/guide 162 (as shown in FIG. 13A), which is along an arc of a circle lying in the plane of the bottom section 126, wherein the circle has its centre point at the connection point 160. The bottom section 126 is movably connected to the first support member 154 by a ball and slot (elongated socket) in a kinematic joint configuration or equivalent other type of connection. Other kinematic joint configurations are also possible so long as they allow motion in some directions and constrain it in others. This connection enables rotation, longitudinal and lateral movement to accommodate the rotation of the couch 114 or bridge. The first support member 154 is prevented from passing through the bottom section 126 because the opening of the slot 162 in the bottom section 126 is smaller than the size of the ball on the top of the first support member. In another example, the slot 162 does not go all the way through the bottom section 126 but is instead only exposed on the underside of the bottom section 126.

The bottom section 126 also comprises an elongated slot/guide 164 located at a portion of the longitudinal centre line of the bottom section 126. The elongated slot 164 is contained within the bottom section 126 and is substantially located at the distal end of the couch 114 but may extend through the plane of the gantry 116 in some configurations. The third support member 158 is movably connected to the bottom section 126. In one example, they are connected by a ball and slot in a kinematic joint configuration but can also be connected by another equivalent joint. The third support member 158 is prevented from passing through the bottom section 126 because the opening of the slot 164 in the bottom section 126 is smaller than the size of the ball on the top of the third support member 158. When the bottom section 126 is rotated (about the connection point 160), the elongated slot 164 enables the third support member 158 to move from a first position to a second position along the longitudinal axis 115 of the couch 114. This movement accommodates the relative longitudinal extension of the bottom section 126 that is caused by the rotation of the couch 114.

Figure 13B:
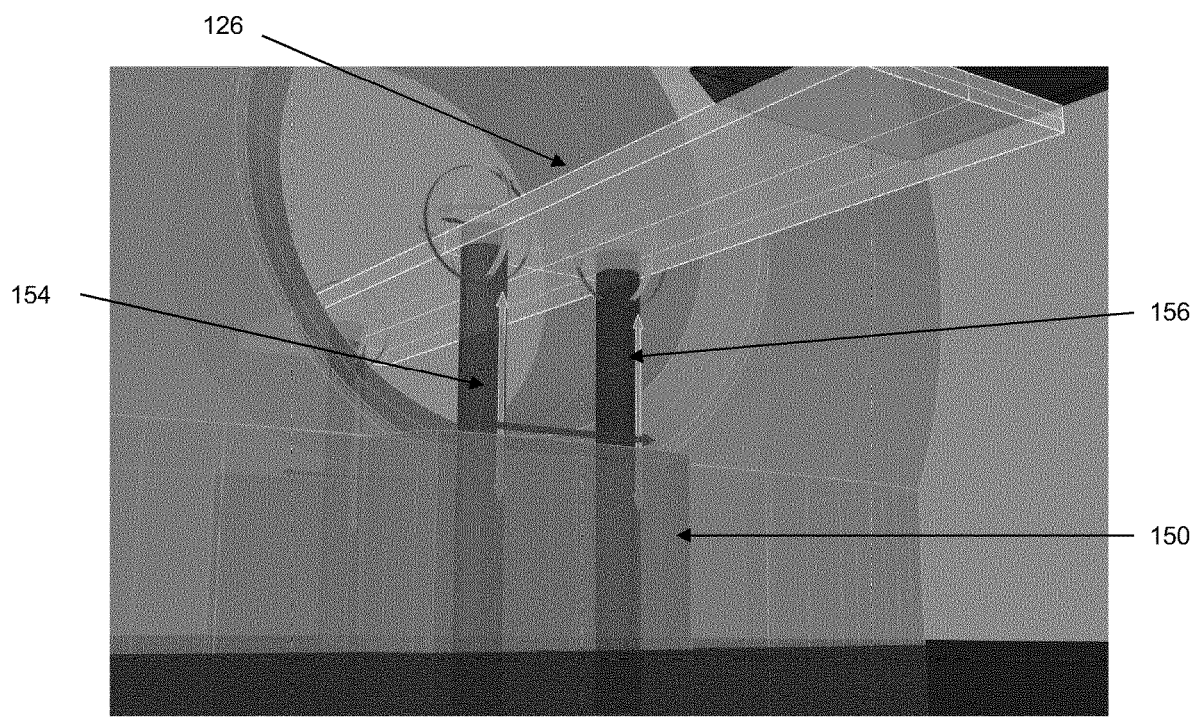
FIG. 13B depicts an isometric view of an embodiment of the radiotherapy device with a rotation mechanism comprising first and second sliding bases as seen viewed from below.

FIG. 13B shows a view from underneath the level of the couch 114 and clearly illustrates the connection between the first sliding base 150, which is set into the floor, and the first and second support members 154, 156. As illustrated by the arrows at the connection points 160, 162, 164, these connections allow 6 degrees of freedom so that the couch 114 can be rotated, tilted and pitched whilst remaining connected to the first, second and third support members 154, 158, 158 at the connection points 160, 162, 164.

Figure 14A:
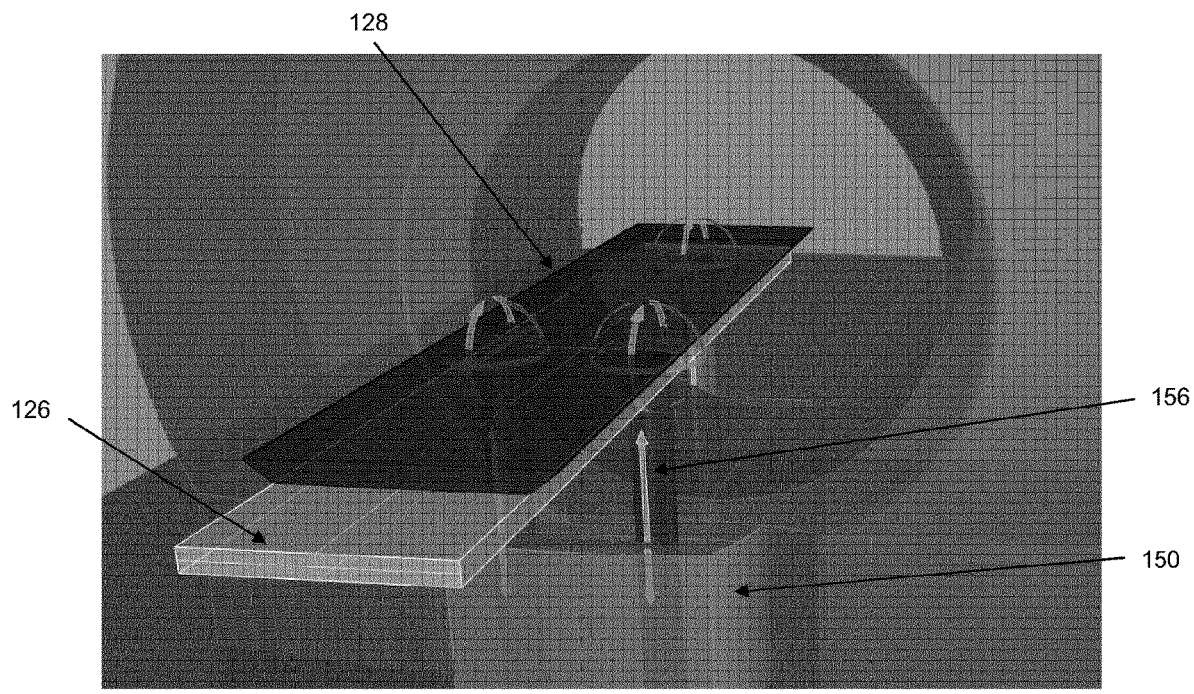
FIG. 14A depicts an isometric view of an embodiment of the radiotherapy device with a rotation mechanism comprising first and second sliding bases, wherein the subject support surface is in a laterally shifted position.
Figure 14B:
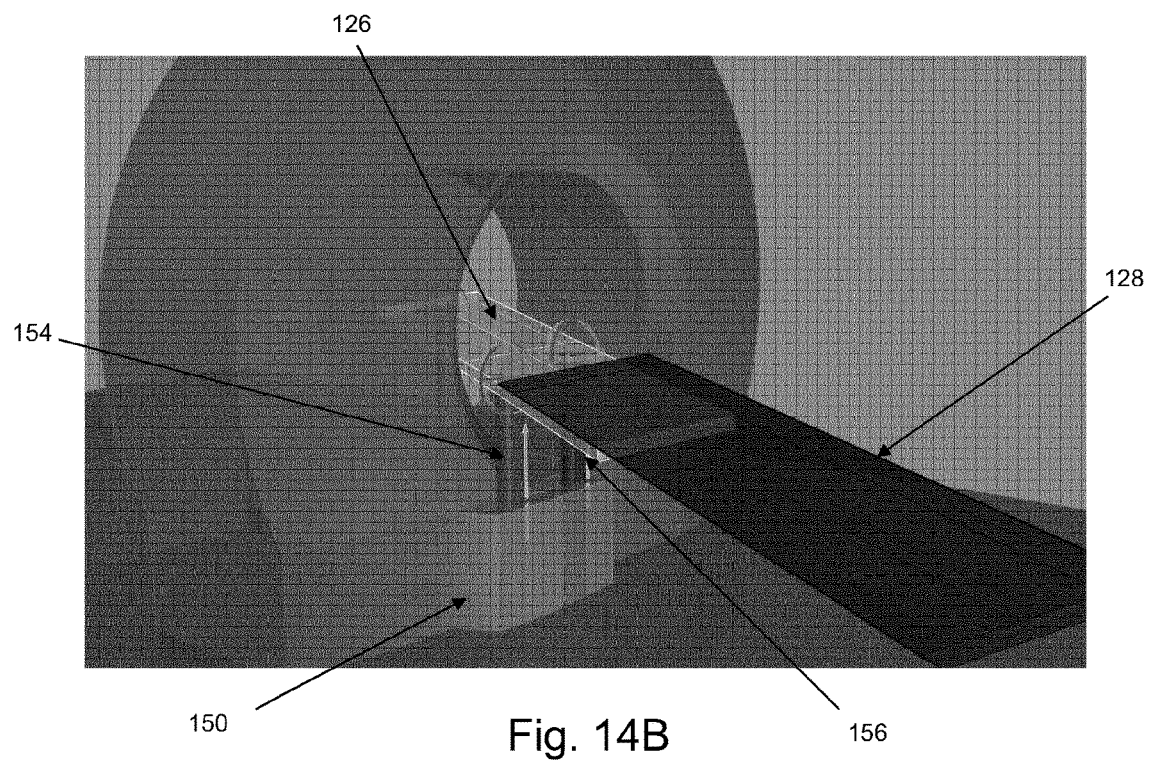
FIG. 14B depicts an isometric view of an embodiment of the radiotherapy device with a rotation mechanism comprising first and second sliding bases with the subject support surface in a rotated position.

The sliding bases 150, 152 can both be moved in sync and in the same direction to produce pure lateral movement of the couch 114, as shown in FIG. 14A. In one example, the lateral movement of the couch 114 can be controlled as part of a treatment plan, and may be controlled in conjunction with a rotation of the couch 114 and/or a movement of the top section 128. The rotation of the couch 114 is driven by the lateral movement of only one of the sliding bases 150, 152, or both of the sliding bases 150, 152 moving in the same direction but at different rates, or both of the sliding bases 150, 152 moving in opposite directions, at the same or different rates, resulting in a rotated configuration as shown in FIG. 14B. The movement of the sliding bases 150, 152 can be at the same time or at different times, whatever the direction. Moving the sliding bases 150, 152 in opposite directions enables the couch 114 to be rotated to the maximum possible angle. For example, if the first sliding member 150 moves in a first direction (along the neutral lateral axis 115) and the second sliding member 152 moves in the opposite direction, this will cause the couch 114 to rotate because it is connected to the second support member 156 at the point 160 and the second support member 156 is connected to the first sliding member 150. The curved slot 162 and the elongated slot 164 are configured to accommodate the rotation of the couch 114. The movement of the sliding bases 150, 152 is controlled by a processor, which can be the same that controls any or all other functions of the apparatus. By controlling the movement of the sliding bases 150, 152, the processor can cause the couch 114 to rotate and can control the effective rotation of the couch 114 by controlling the relative movement of the sliding bases 150, 152. The processor can also control the movement of the couch 114 along the neutral lateral axis 115.

The top section 128 is configured to move from a first position to a second position along at least one of a longitudinal direction 115 and a lateral direction 113. When the couch 114 is rotated by the rotation mechanism 120, as described above, the axis of rotation of the couch 114 passes through the longitudinal axis of the second support member 156, which is itself moved along the neutral lateral axis 113. Accordingly, the rotation mechanism 120 is configured to rotate the couch 114 about an axis of rotation parallel to and spaced from an axis that passes through the isocenter 124. As explained previously, this causes a portion of the couch 114 to move away from the isocenter 124. This can be compensated for by moving the third support member 158, supported by the sliding base 152 in the opposite direction from the movement of the sliding base 150. The lateral movement of the couch 114 can also be used to compensate for the movement of the portion away from the isocenter 124 that is caused by the rotation of the couch 114. The top section 128 can also be used to compensate for the movement of this portion of the couch 114 in such a way as to maintain the portion of the subject support surface 114 substantially at the isocenter 124. The amount of movement required by the top section 128 so as to maintain a portion of the subject support surface 114 substantially at the isocenter 124 is proportional to the rotation and the lateral movement of the couch 114. Accordingly, the top section 128 can be moved in, for example, a longitudinal direction as a function of the rotation of the subject support surface 114 and/or a function of the lateral movement of the couch 114 or a particular one of the sliding bases 150, 152. The movement of the top section 128 of the couch 114 is controlled by a processor as a function of the rotation of subject support surface 114 so as to maintain the portion of the subject support surface 114 substantially at the isocenter 124. In one example, where the neutral longitudinal axis 113 of the couch is initially aligned with the axis of the bore and the rotation of the couch 114 by the rotation mechanism 120 involves moving the first and second sliding bases 150, 152 by an equal amount but in opposite directions, no movement of the top section 128 may be necessary to maintain a particular portion of the couch 114 substantially at the isocenter 124.

The processor is configured to determine the present location of the first and second sliding bases 150, 152 and therefore the position of the first, second and third support members 154, 156, 158, the rotation angle of the couch 114 and the extension/position of the top section 128. The processor can use this information to calculate the amount of compensation that is needed for a particular rotation angle. The processor then instructs the top section 128 to move by the required amount.

As well as controlling the movement of the top section 128 to maintain the portion of the subject support surface 114 substantially at the isocenter 124, it is also possible to control the lateral movement of the rotation mechanism 120 (and thereby the couch 114 itself, which is supported by the rotation mechanism 120) so as to help maintain the portion of the subject support surface 114 substantially at the isocenter 124. As explained previously, this lateral movement can be achieved by moving the two sliding bases 150, 152 in sync in a particular direction. This can be controlled by the processor.

In one example, the processor controls a longitudinal movement of the top section 128 at the same time as a lateral movement of the rotation mechanism 120 both as a function of the rotation angle of the couch 114 in such a way as to maintain a portion of the subject support surface 114 substantially at the isocenter 124.

The first, second and third support members 154, 156, 158 are extendable or retractable in a vertical direction 111. For example, each support member is a telescopic support, which can be extended by any appropriate means, for example an internal screw mechanism, a piston, linear motors or a belt drive. The extension of each of these support members 154, 156, 158 can be controlled independently by the processor. By controlling the extension of these support members 154, 156, 158, the couch 114 can also be rotated around the longitudinal axis 113 of the couch 114 (rolled), and/or rotated about the lateral axis 115 of couch 114 (pivoted). Thus, the processor is configured to control the roll and tilt of the couch 114, which can be controlled as part of a treatment or treatment plan. In this way, it is possible to position a patient 140 with six degrees of freedom. These additional types of rotations can occur whilst the couch is in a neutral rotational position (yaw) or when it is in a rotated position.

Figure 15A:
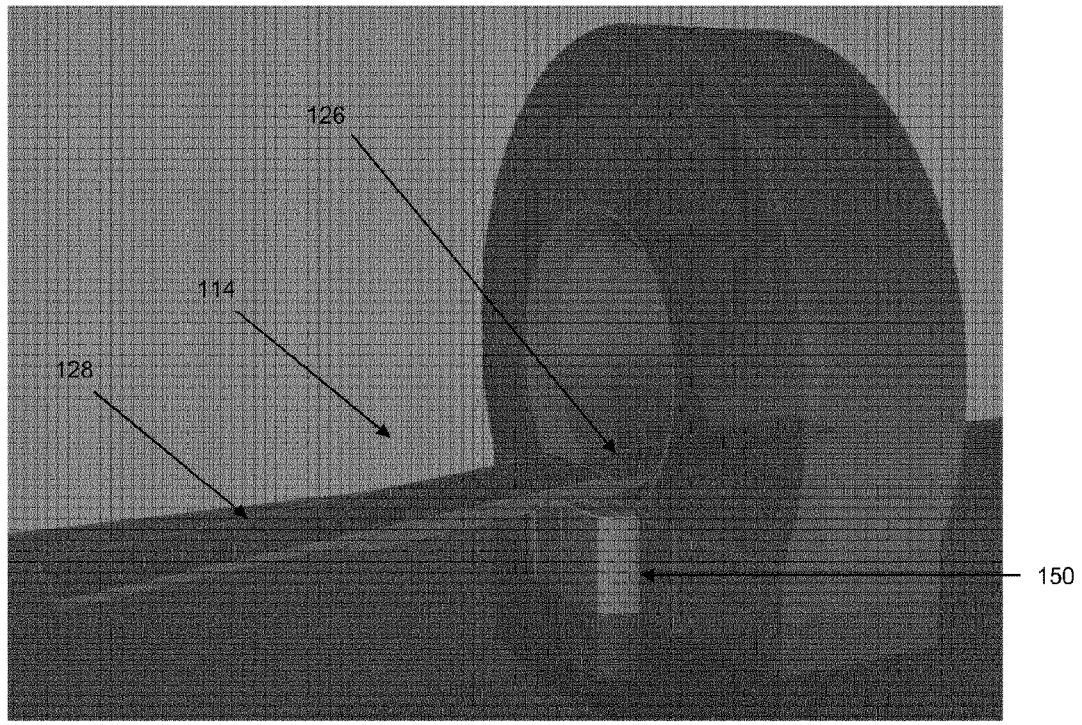
FIG. 15A depicts an isometric view of an embodiment of the radiotherapy device with a rotation mechanism comprising first and second sliding bases with the subject support surface in a pitched position.

For example, as shown in FIG. 15A, the couch 114 can be pitched in such a way that the distal end of the couch 114 is raised and the proximal end of the couch 114 is lowered. This is achieved by extending the third support member 158 at the same time as retracting the first and second support members 154, 156. This can also be combined with an extension/retraction of the top section 128 of the couch 114 so that a part of the couch 114 is lowered beneath the height of the bottom of the bore and so as to enable a patient 140 to more easily climb onto the couch 114 (as shown in FIG. 15A). Pitch can also be used as part of a treatment to help spread the radiation through the healthy tissue, similarly to how this is achieved by rotating the couch 114.

Figure 15B:
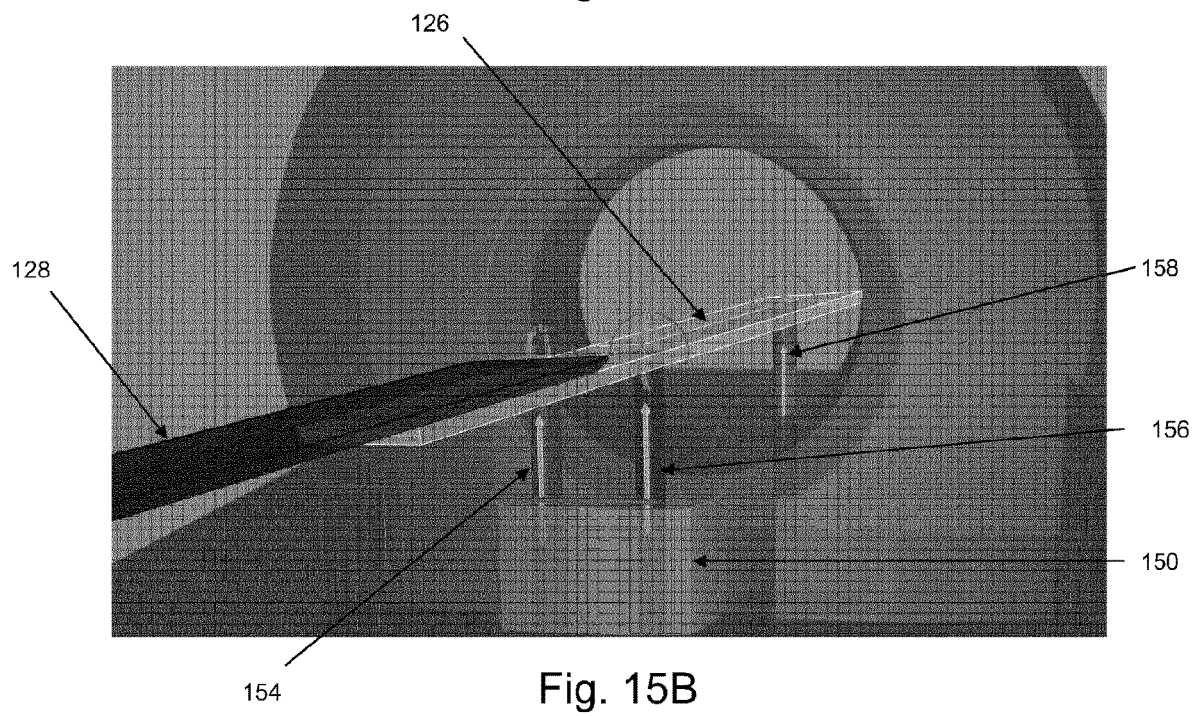
FIG. 15B depicts an isometric view of an embodiment of the radiotherapy device with a rotation mechanism comprising first and second sliding bases with the subject support surface in a rolled position.

For a similar reason, it may be desirable to roll the couch 114 as part of the treatment, as shown in FIG. 15B. This can be achieved by, for example, retracting/lowering the height of the first support member 154 and extending/raising the height of the second support member 156, which will cause the couch 114 to roll towards the first support member 154. This can be performed as part of a treatment, although normally the roll angle will be kept low to maintain patient 140 comfort. In order to accommodate the roll and tilt of the couch 114, the attachment points of the first, second and third support members 154, 156, 158 to the couch 114 are designed to enable such a movement. As described previously, in one example, the attachment point 160 is a ball and socket joint while the other connections are a ball and slot joint, in which the ball if contained within the slot but is free to move along it whilst also allowing for tilt and roll of the couch 114.

In order to control the rotation, pitch and roll of the couch 114 as well as the lateral movement of the couch 114 and the extension of the top section 128, it is necessary for the control system, which may be implemented by the processor, to have feedback regarding the positions/states of the different components including the first and second sliding bases 150, 152, the amount of extension or current height of the first, second and third support members 154, 156, 158 and the position of the top section 128 relative to the bottom section/bridge 126. Therefore, a number of sensors may be used to provide this feedback. For example, an absolute encoder may be used to determine the amount of movement that a particular motor has caused in relation to one of the above measurements. There are many appropriate ways of receiving the feedback of the positions and any suitable means can be used.

The processor may also be configured to use data from a memory that stores information such as the dimensions and configuration of the components so that these can be used in the calculations controlling the movement of the assorted components and to prevent, for example, the couch 114 from colliding with the gantry 116.

It should be noted that the various embodiments may be implemented in hardware, software or a combination thereof. The various embodiments and/or components, for example, components and controllers for these, also may be implemented as part of one or more computers or processors or field-programmable gate arrays (FPGAs). The computer or processor or FPGA may include a computing device, an input device, a display unit and an interface, for example, for accessing the Internet. The computer or processor may include a microprocessor. The microprocessor may be connected to a communication bus. The computer or processor or FPGA may also include a memory. The memory may include Random Access Memory (RAM) and Read Only Memory (ROM). The computer or processor or FPGA further may include a storage device, which may be a hard disk drive or a removable storage drive such as an optical disk drive, and the like. The storage device may also be other similar means for loading computer programs or other instructions into the computer or processor.

The disclosure of this embodiment is only exemplary and there are many variations possible that will result in the same or similar effects, as will be apparent to the skilled person. As one example, whilst the third support member 158 has been described as being in the middle of the second sliding base 152, it could just as well be positioned off centre of the second sliding base 152 and the processor would account for this when controlling the movement. Thus, the above description comprises examples, often preferred examples, of the disclosed embodiments but strict literal compliance with the meaning of the words is not intended and there will be other variations apparent to the skilled person that result in substantially the same effect.

As has been described in the embodiments above, the couch 114 comprises means to allow it to move vertically in relation to the rotation mechanism 120. The means to enable the vertical movement can be comprised within the couch 114, within the rotation mechanism 120 or shared between these. Alternatively, the rotation mechanism 120 itself can be moved in a vertical direction so as to effectively raise or lower the couch 114. The patient support surface 114 can move in any direction.

As well as rotating the couch 114 about a vertical axis 111, the couch 114 or one or more sections 126, 127, 128 of the couch 114 can also be rotated around the longitudinal axis 113 of the couch 114 (rolled), and/or rotated about the lateral axis 115 of couch 114 (pivoted). In this way, it is possible to position a patient 140 with six degrees of freedom. These additional types of rotations can occur whilst the couch is in a neutral rotational position (yaw) or when it is in a rotated position. For reasons of patient 140 comfort and to prevent from them from having to be strapped to the couch 114, the amount of roll and tilt will usually be limited to a small amount, for example, a tilt of 10 degrees forwards or backwards may be used in conjunction with the rotation about the vertical axis 111 that is described more generally herein. In some examples, the couch 114 of section thereof is pitched about an axis that is spaced apart from the isocenter 124 whilst a different section is moved to compensate and maintain a portion of the couch 114 substantially at the isocenter 124. In this way, it is possible to maximise the spread of the radiation through the healthy tissue whilst maximising the dose of radiation that is received at the target region.

The radiation source or gantry 116 itself may also be partially rotated about the transverse axis of the short end of the patient support surface 114 in its neutral position (pitched), although not necessary when the patient support surface 114 is in its neutral position, either at the same time, or a different time, synchronously or separately to the patient support surface 114. This can also be controlled by the same processor as part of a treatment.

The embodiments described above enable use of a couch kick (rotatable couch 114) in a ring gantry based linac system. It effectively provides isocentric couch rotation but without requiring physical rotation about the isocenter 124.

If a section of the couch was not moved as a function of the rotation of the couch 114 (given that the rotation is not about the isocenter 124), then the location of the target region would move with respect to the isocenter 124 (and focus of the radiation) and, accordingly, this would result in an increased dosage of radiation being received by healthy tissue. Furthermore, this would result in a longer treatment time because the target region would not receive the intended dosage of radiation. By rotating the couch 114 and hence the patient 140, whilst maintaining a particular portion substantially at the isocenter 124, the radiation dose can be spread through the healthy tissue so that the radiation dose received by healthy tissue surrounding a target region is minimised.

The invention claimed is:

1. A radiotherapy apparatus for delivering radiation to a subject, the apparatus comprising:
    a source of radiation configured to rotate about an isocenter and emit radiation in a radiation plane containing said isocenter;
    a subject support surface including a portion configured to be located substantially at the isocenter, the subject support surface comprising:
    a subject support surface rotation mechanism configured to rotate the subject support surface about an axis of rotation parallel to and spaced apart from an axis that passes through the isocenter, wherein the rotation mechanism is distributed on both sides of the radiation plane, and wherein the subject support surface rotation mechanism is connected to: a proximal end of the subject support surface on one side of the radiation plane and a distal end of the subject support surface on one side of the radiation plane;
    a first section configured to move from a first position to a second position along at least one of a longitudinal direction or a lateral direction; and
    a processor configured to control at least one of longitudinal movement or lateral movement of the first section as a function of the rotation of the subject support surface to maintain the portion of the subject support surface substantially at the isocenter.

2. The radiotherapy apparatus of claim 1, wherein the axis of rotation is at least one of a longitudinal axis, a transverse axis or a vertical axis.

3. The radiotherapy apparatus of claim 1, wherein the rotation mechanism is located outside the radiation plane.

4. The radiotherapy apparatus of claim 1, wherein the subject support surface is additionally configured to move from a first position to a second position along a vertical direction.

5. The radiotherapy apparatus of claim 1, wherein the subject support surface comprises a second section, wherein the second section is configured to move from a first position to a second position along at least one of a longitudinal direction or a lateral direction, and wherein the processor is configured to control movement of the first section and the second section as a function of the rotation of the subject support surface to maintain the portion of the subject support surface substantially at the isocenter.

6. The radiotherapy apparatus of claim 1, wherein the rotation mechanism comprises:
    a first sliding base indirectly connected to the proximal end of the subject support surface and configured to move from a first position to a second position along a lateral direction; and
    a second sliding base connected to the distal end of the subject support surface and configured to move from a first position to a second position along a lateral direction, wherein the processor is configured to control the lateral movement of the first sliding base and the second sliding base to at least one of rotate the subject support surface or to move the rotation mechanism in a lateral direction, and wherein the processor is configured to control the lateral movement of the rotation mechanism as a function of the rotation of the rotation of the subject support surface to maintain the portion of the subject support surface at the isocenter.

7. The radiotherapy apparatus of claim 6, wherein the rotation mechanism comprises one or more extendable support members, and wherein the processor is configured to selectively extend the one or more extendable support members to control at least one of a roll or a pitch of the subject support surface.

8. The radiotherapy apparatus of claim 1, wherein the subject support surface rotation mechanism is configured to rotate the subject support surface+/−30 degrees about the subject support surface axis of rotation.

9. A method for controlling a subject support surface in a radiotherapy apparatus comprising a source of radiation configured to rotate about an isocenter and emit radiation in a radiation plane containing said isocenter, the method comprising:
    providing a subject support surface configured such that a portion of the subject support surface is located substantially at the isocenter;
    rotating the subject support surface using a subject support surface rotation mechanism about an axis of rotation parallel to and spaced apart from an axis that passes through the isocenter, wherein the rotation mechanism is distributed on both sides of the radiation plane, and wherein the rotation mechanism is connected to: a proximal end of the subject support surface on one side of the radiation plane and a distal end of the subject support surface on one side of the radiation plane; and
    moving a first section of the subject support surface from a first position to a second position along at least one of a longitudinal or a lateral direction as a function of the rotation of the subject support surface to maintain the portion of the subject support surface substantially at the isocenter.

10. The method of claim 9; additionally comprising:
    moving the subject support surface from a first position to a second position along a vertical direction.

11. The method of claim 9, additionally comprising:
    moving a second section of the subject support surface from a first position to a second position along at least one of a longitudinal or a lateral direction.

12. The method of claim 11, additionally comprising:
    controlling movement of the first second and the second section as a function of the rotation of the subject support surface to maintain the portion of the subject support surface substantially at the isocenter.

13. A non-transitory computer-readable storage medium comprising instructions which, when executed by a processor of a computer, cause the processor to:
    rotate a subject support surface of a radiotherapy apparatus configured to rotate, using a subject support surface rotation mechanism, about an isocenter and emit radiation in a radiation plane containing the isocenter, and about an axis of rotation parallel to and spaced apart from an axis that passes through the isocenter, wherein a portion of the subject support surface is located substantially at the isocenter, wherein the subject support surface rotation mechanism is distributed on both sides of the radiation plane, and wherein the rotation mechanism is connected to: a proximal end of the subject support surface on one side of the radiation plane and a distal end of the subject support surface on one side of the radiation plane; and move a first section of the subject support surface from a first position to a second position along at least one of a longitudinal or a lateral direction as a function of the rotation of the subject support surface to maintain the portion of the subject support surface substantially at the isocenter.

* * * * *